United States Patent
Jeon et al.

(10) Patent No.: US 11,345,901 B2
(45) Date of Patent: May 31, 2022

(54) ACETOHYDROXY ACID SYNTHASE VARIANT AND A MICROORGANISM COMPRISING THE SAME

(71) Applicant: CJ CHEILJEDANG CORPORATION, Seoul (KR)

(72) Inventors: Ae Ji Jeon, Seoul (KR); Byeong Cheol Song, Yongin-si (KR); Ji Hye Lee, Anyang-si (KR); Jong Hyun Kim, Suwon-si (KR); Hye Won Kim, Seongnam-si (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 17/357,196

(22) Filed: Jun. 24, 2021

(65) Prior Publication Data

US 2021/0324349 A1  Oct. 21, 2021

Related U.S. Application Data

(62) Division of application No. 17/076,057, filed on Oct. 21, 2020, now Pat. No. 11,085,029, which is a division of application No. 16/479,813, filed as application No. PCT/KR2018/007821 on Jul. 10, 2018, now Pat. No. 10,844,359.

(30) Foreign Application Priority Data

Jul. 11, 2017 (KR) .......................... 10-2017-0087978

(51) Int. Cl.
  *C12N 9/10*   (2006.01)
  *C12P 13/06*  (2006.01)
  *C12P 13/08*  (2006.01)

(52) U.S. Cl.
  CPC ............ *C12N 9/1022* (2013.01); *C12P 13/06* (2013.01); *C12P 13/08* (2013.01); *C12Y 202/01006* (2013.01)

(58) Field of Classification Search
  CPC ........ C12N 9/1022; C12P 13/08; C12P 13/06; C12Y 202/01006
  See application file for complete search history.

(56) References Cited

U.S. PATENT DOCUMENTS

| | | | |
|---|---|---|---|
| 7,323,321 B2 | 1/2008 | Rayapati et al. | |
| 7,332,310 B2 | 2/2008 | Nakagawa et al. | |
| 7,635,579 B2 | 12/2009 | Rayapati et al. | |
| 2009/0205064 A1 | 8/2009 | Schopke et al. | |
| 2010/0086966 A1 | 4/2010 | Patek et al. | |
| 2011/0053777 A1 | 3/2011 | Oard et al. | |
| 2014/0335574 A1 | 11/2014 | Sycheva et al. | |
| 2016/0115506 A1 | 4/2016 | Gerstmeir et al. | |
| 2017/0226488 A1 | 8/2017 | Jeon et al. | |

FOREIGN PATENT DOCUMENTS

| CN | 102286505 A | 12/2011 |
|---|---|---|
| CN | 106754807 A | 5/2017 |
| KR | 10-2006-0024437 A | 3/2006 |
| KR | 10-2008-0025355 A | 3/2008 |
| KR | 10-1117022 | 3/2012 |
| KR | 10-1720836 | 4/2017 |
| WO | 2013/027709 | 2/2013 |
| WO | 2014/142463 | 9/2014 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Chipman et al., "Biosynthesis of 2-aceto-2-hydroxy acids: acetolactate synthases and acetohydroxyacid synthases," *Biochimica et Biophysica Acta* 1385:401-419, 1998,.
GenBank: M10313.1, "E.coli ilv gene cluster encoding ilvD and ilvA peptides, acetohydroxy acid syntl branched-chain amino acid aminotransferase, complete cds," 6 pages (May 20, 1994).
Gedi et al., "Bacterial acetohydroxyacid synthase and its inhibitors—a summary of their structure, biological activity and current status" *FEBS Journal* 279:946-963 (2012),.
Guo et al., "Analysis of acetohydroxyacid synthase variants from branched-chain amino acids-producing strains and their effect on the synthesis of branched-chain amino acids in Corynebacterium glutamicum," *Protein Expression and Purification* 109:106-112, 2015.
Ibdah et al., "Homology Modeling of the Structure of Bacterial Acetohydroxy Acid Synthase and Examination of the Active Site by Site-Directed Mutagenesis," *Biochemistry* 35:16282-16291, 1996.
NCBI Reference Sequence: WP_003861429.1, (Oct. 1, 2015).

* cited by examiner

*Primary Examiner* — Delia M Ramirez
(74) *Attorney, Agent, or Firm* — Seed IP Law Group LLP

(57) ABSTRACT

The present disclosure relates to a novel acetohydroxy acid synthase, a microorganism comprising the same, or a method for producing an L-branched-chain amino acid using the same.

6 Claims, No Drawings
Specification includes a Sequence Listing.

— 1 —

ACETOHYDROXY ACID SYNTHASE VARIANT AND A MICROORGANISM COMPRISING THE SAME

CROSS REFERENCE TO RELATED APPLICATIONS

The present application is a divisional application of U.S. application Ser. No. 17/076,057 filed Oct. 21, 2020, now U.S. Pat. No. 11,085,029, which is a divisional of U.S. application Ser. No. 16/479,813 filed Jul. 22, 2019, now U.S. Pat. No. 10,844,359, which is a U.S. national phase application of PCT/KR2018/007821, filed Jul. 10, 2018, which claims priority to KR Application No. 10-2017-0087978, filed Jul. 11, 2017. U.S. application Ser. Nos. 16/479,813 and 17/076,057 are herein incorporated by reference in their entity.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_4149D3_SEQUENCE_LISTING.txt. The text file is 59 KB, was created on Jun. 23, 2021, and is being submitted electronically via EFS-Web.

TECHNICAL FIELD

The present disclosure relates to a novel acetohydroxy acid synthase variant and a use thereof, and specifically, to an acetohydroxy acid synthase variant, a microorganism containing the variant, or a method for producing an L-branched-chain amino acid.

BACKGROUND ART

Branched-chain amino acids (e.g., L-valine, L-leucine, and L-isoleucine) are known to increase protein levels in an individual and have an important role as an energy source during exercise, and thus are widely used in medicines, foods, etc. With regard to the biosynthesis of branched-chain amino acids, the same enzymes are used in parallel biosynthesis pathways, and thus it is difficult to produce a single kind of branched-chain amino acid on an industrial scale via fermentation. In the preparation of branched-chain amino acids, the role of acetohydroxy acid synthase (i.e., the first enzyme in the biosynthesis of branched-chain amino acids) is most important; however, previous studies on acetohydroxy acid synthase were mainly focused on release of feedback inhibition due to modifications of acetohydroxy acid synthase small subunit (IlvN protein) (*Protein Expr Purif.* 2015 May; 109:106-12, US2014-0335574, US2009-496475, US2006-303888, US2008-245610), thus revealing a serious lack of relevant studies.

Acetohydroxy acid synthase is an enzyme which has roles of producing acetolactic acid from two molecules of pyruvate and producing 2-aceto-2-hydroxy-butyrate from ketobutyric acid and pyruvate. The acetohydroxy acid synthase catalyzes decarboxylation of pyruvate and a condensation reaction with another pyruvate molecule to produce acetolactate, which is a precursor of valine and leucine; or catalyzes decarboxylation of pyruvate and a condensation reaction with 2-ketobutyrate to produce acetohydroxybutyrate, which is a precursor of isoleucine. Accordingly, acetohydroxy acid synthase is a very important enzyme involved in the initial biosynthesis process of L-branched-chain amino acids.

DISCLOSURE

Technical Problem

The present inventors have made efforts for effective production of L-branched-chain amino acids, and as a result, they have developed a large subunit variant. Then, the present inventors confirmed that L-branched-chain amino acids can be produced in high yield from a microorganism containing the variant, thereby completing the present disclosure.

Technical Solution

An object of the present disclosure is to provide an acetohydroxy acid synthase variant.

Another object of the present disclosure is to provide a polynucleotide encoding the acetohydroxy acid synthase variant, a vector containing the polynucleotide, and a transformant in which the vector is introduced.

Still another object of the present disclosure is to provide a microorganism producing an L-branched-chain amino acid, in which the microorganism contains the acetohydroxy acid synthase variant or into which the vector is introduced.

Still another object of the present disclosure is to provide a method for producing an L-branched-chain amino acid, which includes: culturing the microorganism producing the L-branched-chain amino acid in a medium; and recovering the L-branched-chain amino acid from the microorganism or cultured medium thereof.

Advantageous Effects

When the activity of the acetohydroxy acid synthase variant according to the present disclosure is introduced into a microorganism, the microorganism can significantly increase the ability to produce an L-branched-chain amino acid. Therefore, the microorganism can be widely used for large-scale production of L-branched-chain amino acids.

BEST MODE

To achieve the above objects, an aspect of the present disclosure provides an acetohydroxy acid synthase variant, in which, in the acetohydroxy acid synthase large subunit (i.e., acetolactate synthase large subunit; IlvB protein), the $96^{th}$ amino acid (i.e., threonine) is substituted with an amino acid other than threonine, the 503rd amino acid (i.e., tryptophan) is substituted with an amino acid other than tryptophan, or both the $96^{th}$ amino acid (i.e., threonine) and the $503^{rd}$ amino acid (i.e., tryptophan) are substituted with another amino acid.

Specifically, the large subunit of the acetohydroxy acid synthase may have an amino acid sequence of SEQ ID NO: 1. More specifically, the acetohydroxy acid synthase variant may be an acetohydroxy acid synthase variant, in which, in the amino acid sequence of SEQ ID NO: 1, the $96^{th}$ amino acid (i.e., threonine) or the 503rd amino acid (i.e., tryptophan) from the N-terminus thereof is substituted with another amino acid; or both the $96^{th}$ amino acid (i.e., threonine) and the $503^{rd}$ amino acid (i.e., tryptophan) are each substituted with another amino acid.

As used herein, the term "acetohydroxy acid synthase" refers to an enzyme involved in the biosynthesis of L-branched-chain amino acids, and it may be involved in the first step of the biosynthesis of L-branched-chain amino acids. Specifically, acetohydroxy acid synthase may catalyze decarboxylation of pyruvate and a condensation reaction with another pyruvate molecule to produce acetolactate (i.e., a precursor of valine) or may catalyze decarboxylation of pyruvate and a condensation reaction with 2-ketobutyrate to produce acetohydroxybutyrate (i.e., a precursor of isoleucine). Specifically, starting from acetolactic acid, L-valine is biosynthesized by sequential reactions catalyzed by acetohydroxy acid isomeroreductase, dihydroxy acid dehydratase, and transaminase B. Additionally, starting from acetolactic acid, L-leucine is biosynthesized as a final product by sequential reactions catalyzed by acetohydroxy acid isomeroreductase, dihydroxy acid dehydratase, 2-isopropylmalate synthase, isopropylmalate isomerase, 3-isopropylmalate dehydrogenase, and transaminase B. Meanwhile, starting from acetohydroxybutyrate, L-isoleucine is biosynthesized as a final product by sequential reactions catalyzed by acetohydroxy acid isomeroreductase, dihydroxy acid dehydratase, and transaminase B. Accordingly, acetohydroxy acid synthase is an important enzyme in the biosynthesis pathway of L-branched-chain amino acids.

Acetohydroxy acid synthase is encoded by two genes, i.e., ilvB and ilvN. The ilvB gene encodes the large subunit of acetohydroxy acid synthase (IlvB), and the ilvN gene encodes the small subunit of acetohydroxy acid synthase (IlvN).

In the present disclosure, the acetohydroxy acid synthase may be one derived from a microorganism of the genus *Corynebacterium*, and specifically from *Corynebacterium glutamicum*. More specifically, as the large subunit of the acetohydroxy acid synthase, any protein having the IlvB protein activity and a homology or identity of 70% or higher, specifically 80% or higher, more specifically 85% or higher, even more specifically 90% or higher, and even yet more specifically 95%, to the amino acid sequence of SEQ ID NO: 1 as well as the amino acid sequence of SEQ ID NO: 1, may be included without limitation. Additionally, due to codon degeneracy, the polynucleotide encoding the protein having the IlvB protein activity may be modified variously in the coding region within a range that does not alter the amino acid sequence of the protein expressed from the coding region, considering the codons preferred in the organism for which the protein is to be expressed. The nucleotide sequence may be included without limitation as long as it encodes the amino acid sequence of SEQ ID NO: 1, and specifically, it may be one encoded by the nucleotide sequence of SEQ ID NO: 2.

As used herein, the term "acetohydroxy acid synthase variant" refers to a protein in which one or more amino acids are modified (e.g., added, deleted, or substituted) in the amino acid sequence of the acetohydroxy acid synthase protein. Specifically, the acetohydroxy acid synthase variant is a protein in which its activity is effectively increased compared to its wild-type or before modification due to the modification of the present disclosure.

As used herein, the term "modification" refers to a common method for improving enzymes, and any method known in the art may be used without limitation, including strategies such as rational design and directed evolution. For example, the strategies for rational design include a method for specifying an amino acid at a particular position (site-directed mutagenesis or site-specific mutagenesis), etc., and the strategies for directed evolution include a method for inducing random mutagenesis, etc. Additionally, the modification may be one induced by natural mutation without external manipulation. Specifically, the acetohydroxy acid synthase variant may be one which is isolated, a recombinant protein, or one which has occurred non-naturally, but the acetohydroxy acid synthase variants are not limited thereto.

The acetohydroxy acid synthase variant of the present disclosure may be specifically an IlvB protein having an amino acid sequence of SEQ ID NO: 1, in which the $96^{th}$ amino acid (threonine) or the $503^{rd}$ amino acid (tryptophan) from the N-terminus thereof is mutated; or both the $96^{th}$ amino acid (threonine) and the $503^{rd}$ amino acid (tryptophan) are simultaneously substituted with another amino acid, but the acetohydroxy acid synthase variant is not limited thereto. For example, the acetohydroxy acid synthase variant of the present disclosure may be an IlvB protein, in which the $96^{th}$ amino acid (threonine) is substituted with serine, cysteine, or alanine, or the $503^{rd}$ amino acid (tryptophan) is substituted with glutamine, asparagine, or leucine. Additionally, it is apparent that any acetohydroxy acid synthase variant which has an amino acid sequence in which the $96^{th}$ amino acid or the $503^{rd}$ amino acid is substituted with another amino acid, and simultaneously, part of the amino acid sequence is deleted, modified, substituted, or added, may exhibit an activity which is identical or corresponding to that of the acetohydroxy acid synthase variant of the present disclosure.

Furthermore, the large subunits themselves of the acetohydroxy acid synthase variants with the modifications described above, acetohydroxy acid synthase including the large subunits of the acetohydroxy acid synthase variants, and acetohydroxy acid synthase including both the large and small subunits of the acetohydroxy acid synthase variants may all be included in the scope of the acetohydroxy acid synthase variant of the present disclosure, but the acetohydroxy acid synthase variant is not limited thereto.

In the present disclosure, it was confirmed that the amount of L-branched-chain amino acid production can be increased by the substitution of the $96^{th}$ amino acid and the $503^{rd}$ amino acid of the acetohydroxy acid synthase protein with various other amino acids, and thus it was confirmed that amino acid positions at 96 and 503 are important in the modification of the acetohydroxy acid synthase protein in connection with the L-branched-chain amino acid production. However, since the substituted amino acids in embodiments of the present disclosure are merely representative embodiments showing the effects of the present disclosure, the scope of the present disclosure should not be limited to these embodiments, and it is apparent that when the $96^{th}$ amino acid (threonine) is substituted with an amino acid other than threonine, the $503^{rd}$ amino acid (tryptophan) is substituted with an amino acid other than tryptophan, or both the $96^{th}$ amino acid and the $503^{rd}$ amino acid are substituted with a different amino acid, the acetohydroxy acid synthase variants may have effects corresponding to those described in embodiments.

Additionally, the acetohydroxy acid synthase variant of the present disclosure may have an amino acid sequence represented by any one of SEQ ID NOS: 28 to 33, but the amino acid sequence of the acetohydroxy acid synthase variant is not limited thereto. Additionally, any polypeptide which has a homology or identity of at least 70%, at least 80%, at least 85%, at least 90%, at least 95%, or at least 99% to the above amino acid sequences may also be included without limitation, as long as these polypeptides have an activity substantially identical or corresponding to that of the acetohydroxy acid synthase variant by including the modifications of the present disclosure.

Homology and identity refer to a degree of relatedness between two given amino acid sequences or nucleotide sequences and may be expressed as a percentage.

The terms "homology" and "identity" may often be used interchangeably with each other.

Sequence homology or identity of a conserved polynucleotide or polypeptide may be determined by a standard alignment algorithm, and default gap penalties established by a program to be used may be used in combination. Substantially, homologous or identical sequences may hybridize under moderately or highly stringent conditions along their entire sequence or at least about 50%, about 60%, about 70%, about 80%, or about 90% of the entire length. With regard to the polynucleotides to be hybridized, polynucleotides including a degenerate codon instead of a codon may also be considered.

Whether any two polynucleotide or polypeptide sequences have homology, similarity, or identity may be determined by, for example, a known computer algorithm such as the "FASTA" program using default parameters as in Pearson et al. (1988) (*Proc. Natl. Acad. Sci. USA* 85]: 2444). Alternatively, they may be determined using the Needleman-Wunsch algorithm (Needleman and Wunsch, 1970, *J. Mol. Biol.* 48: 443 to 453) as performed in the Needleman program of the EMBOSS package (EMBOSS: The European Molecular Biology Open Software Suite, Rice et al., 2000, *Trends Genet.* 16: 276 to 277) (version 5.0.0 or later) (including GCG program package (Devereux, J., et al., *Nucleic Acids Research* 12: 387 (1984)), BLASTP, BLASTN, FASTA (Atschul, [S.] [F.] et al., *J Molec Biol* 215]: 403 (1990); Guide to Huge Computers, Martin J. Bishop, [ED.,] Academic Press, San Diego, 1994, and [CARILLO ETA/.](1988) *SIAM J Applied Math* 48: 1073). For example, homology, similarity, or identity may be determined using BLAST or ClustalW of the National Center for Biotechnology Information.

Homology, similarity, or identity of polynucleotides or polypeptides may be determined by comparing sequence information using the GAP computer program (e.g., Needleman et al. (1970), *J Mol Biol* 48: 443) as disclosed in Smith and Waterman, *Adv. Appl. Math* (1981) 2:482. Briefly, the GAP program defines similarity as the number of aligned symbols (i.e., nucleotides or amino acids) which are similar, divided by the total number of symbols in the shorter of the two sequences. The default parameters for the GAP program may include: (1) a unary comparison matrix (containing a value of 1 for identities and 0 for non-identities) and the weighted comparison matrix (or EDNAFULL (EMBOSS version of NCBI NUC4.4) substitution matrix) of Gribskov et al. (1986) *Nucl. Acids Res.* 14: 6745, as disclosed by Schwartz and Dayhoff, eds., Atlas Of Protein Sequence And Structure, National Biomedical Research Foundation, pp. 353 to 358 (1979); (2) a penalty of 3.0 for each gap and an additional 0.10 penalty for each symbol in each gap (or gap open penalty 10, gap extension penalty 0.5); and (3) no penalty for end gaps. Therefore, the term "homology" or "identity", as used herein, represents relevance between sequences.

Another aspect of the present disclosure provides a polynucleotide encoding the acetohydroxy acid synthase variant of the present disclosure.

As used herein, the term "polynucleotide" has a meaning to include a DNA or RNA molecule, and a nucleotide, which is a basic building block thereof, includes not only a natural nucleotide but also an analog in which a saccharide or base region is modified. In the present disclosure, the polynucleotide may be a polynucleotide isolated from a cell or an artificially synthesized polynucleotide, but the polynucleotide is not limited thereto.

The polynucleotide encoding the acetohydroxy acid synthase variant of the present disclosure may include without limitation any nucleotide sequence that encodes the protein having an activity of the acetohydroxy acid synthase variant of the present disclosure. Specifically, due to codon degeneracy or in consideration of the codons preferred by a microorganism in which the protein is to be expressed, various modifications may be made in the coding region of the protein within the scope that does not change the amino acid sequence of the protein. The polynucleotide may include without limitation any nucleotide sequence encoding the amino acid sequence of SEQ ID NOS: 28 to 33, and specifically, one having the nucleotide sequence of SEQ ID NOS: 34 to 39. Additionally, any polypeptide which has a homology or identity of at least 70%, at least 75%, at least 80%, at least 85%, at least 90%, at least 95%, at least 97%, or at least 99% to the above amino acid sequences may also be included without limitation, as long as these polypeptides have an activity substantially identical or corresponding to that of the acetohydroxy acid synthase variant by including the modifications of the present disclosure due to codon degeneracy.

Alternatively, by hybridization under stringent conditions with a probe that can be prepared from a known gene sequence (e.g., a sequence complementary to all or part of the nucleotide sequence), any sequence encoding a protein having the activity of the proteins consisting of the amino acid sequence of SEQ ID NOS: 28 to 33 may be included without limitation.

The "stringent conditions" refer to conditions that enable specific hybridization between polynucleotides. Such conditions are described in detail in the literature (e.g., J. Sambrook et al., supra). The stringent conditions may include conditions under which genes having high homology or identity (e.g., genes having at least 80%, specifically at least 85%, more specifically at least 90%, even more specifically at least 95%, even yet more specifically at least 97%, or most specifically at least 99%) can hybridize to each other; conditions under which genes having lower homology or identity cannot hybridize to each other; or conditions which are common washing conditions for Southern hybridization (e.g., a salt concentration and a temperature corresponding to 60° C., 1×SSC, 0.1% SDS; specifically 60° C., 0.1×SSC, 0.1% SDS; more specifically 68° C., 0.1×SSC, 0.1% SDS, once, specifically, twice or three times).

Hybridization requires that two nucleic acids have complementary sequences, although mismatches between bases may be possible depending on hybridization stringency. The term "complementary" is used to describe the relationship between nucleotide bases that can hybridize to each another. For example, with respect to DNA, adenosine is complementary to thymine, and cytosine is complementary to guanine. Accordingly, the present disclosure may also include isolated nucleic acid fragments complementary to the entire sequence as well as to substantially similar nucleic acid sequences.

Specifically, a polynucleotide having homology or identity may be detected using hybridization conditions including a hybridization step at $T_m$ of 55° C. and by utilizing the above-described conditions. Additionally, the $T_m$ value may be 60° C., 63° C., or 65° C., but is not limited thereto, and may be appropriately controlled by those skilled in the art according to the purpose. The appropriate stringency for hybridizing polynucleotides depends on the length of the polynucleotides and the degree of complementarity, and variables are well known in the art (see Sambrook et al., supra, 9.50 to 9.51, 11.7 to 11.8).

Still another aspect of the present disclosure provides a vector including the polynucleotide encoding the modified acetohydroxy acid synthase variant of the present disclosure.

As used herein, the term "vector" refers to any carrier for cloning and/or transferring nucleotides into a host cell. A vector may be a replicon to allow for the replication of a fragment(s) combined with other DNA fragment(s). "Replicon" refers to any genetic unit functioning as a self-replicating unit for DNA replication in vivo, that is, replicable by self-regulation. Specifically, the vector may be plasmids, phages, cosmids, chromosomes, or viruses in a natural or recombined state. For example, as a phage vector or cosmid vector, pWE15, M13, λMBL3, λMBL4, λIXII, λASHII, λAPII, λt10, λt11, Charon4A, Charon21A, etc. may be used, and as a plasmid vector, those based on pBR, pUC, pBluescriptll, pGEM, pTZ, pCL, pET, etc. may be used. The vectors that can be used in the present disclosure are not particularly limited, but any known expression vector may be used. Additionally, the vector may include a transposon or artificial chromosome.

In the present disclosure, the vector is not particularly limited as long as it includes a polynucleotide encoding the acetohydroxy acid synthase variant of the present disclosure. The vector may be one which can replicate and/or express the nucleic acid molecule in eukaryotic or prokaryotic cells including mammalian cells (e.g., cells of humans, monkeys, rabbits, rats, hamsters, mice, etc.), plant cells, yeast cells, insect cells, and bacteria cells (e.g., *E. coli*, etc.), and specifically, may be one which is operably linked to a suitable promoter so that the polynucleotide can be expressed in a host cell and include at least one selectable marker.

Additionally, as used herein, the term "operably linked" refers to a functional connection between a promoter sequence, which initiates and mediates the transcription of the polynucleotide encoding the target protein of the present disclosure, and the above gene sequence.

Still another aspect of the present disclosure provides a transformant into which the vector of the present disclosure is introduced.

In the present disclosure, the transformant may be any transformable cell into which the above vector can be introduced and in which the acetohydroxy acid synthase variant of the present disclosure can be expressed. Specifically, the transformant may be any transformed cells of bacteria belonging to the genus *Escherichia*, the genus *Corynebacterium*, the genus *Streptomyces*, the genus *Brevibacterium*, the genus *Serratia*, the genus *Providencia, Salmonella typhimurium*, etc.; cells of yeasts; fungal cells of *Pichia pastoris*, etc.; transformed cells of insects (e.g., *Drosophila, Spodoptera* Sf9, etc.); and transformed animal cells (e.g., cells of Chinese hamster ovary (CHO), SP2/0 (mouse myeloma), human lymphoblastoid, COS, NSO (mouse myeloma), 293T, bow melanoma, HT-1080, baby hamster kidney (BHK), human embryonic kidney (HEK), PERC.6 (human retinocytes)); or transformed plant cells, but the transformant is not particularly limited thereto.

Still another aspect of the present disclosure provides a microorganism producing L-branched chain amino acids, in which the microorganism contains the acetohydroxy acid synthase variant or into which a vector containing a polynucleotide encoding the variant is introduced.

As used herein, the term "L-branched-chain amino acid" refers to an amino acid with a branched alkyl group on the side chain, and it includes valine, leucine, and isoleucine. Specifically, in the present disclosure, the L-branched-chain amino acid may be L-valine or L-leucine, but is not limited thereto.

As used herein, the term "microorganism" includes all of a wild-type microorganism and a naturally or artificially genetically modified microorganism, and it is a concept including all of the microorganisms in which a particular mechanism is attenuated or enhanced due to insertion of an exogenous gene or enhancement or attenuation of activity of an endogenous gene. The microorganism refers to all of the microorganisms that can express the acetohydroxy acid synthase variant of the present disclosure. Specifically, the microorganism may be *Corynebacterium glutamicum, Corynebacterium ammoniagenes, Brevibacterium lactofermentum, Brevibacterium flavum, Corynebacterium thermoaminogenes, Corynebacterium efficiens*, etc., and more specifically *Corynebacterium glutamicum*, but the microorganism is not limited thereto.

As used herein, the term "microorganism producing L-branched-chain amino acids" may refer to a natural microorganism or a modified microorganism which has the ability to produce L-branched-chain amino acids via modification, and specifically may refer to a non-naturally occurring recombinant microorganism, but the microorganism is not limited thereto. The microorganism producing L-branched-chain amino acids is a microorganism which contains the acetohydroxy acid synthase variant of the present disclosure or into which a vector containing a polynucleotide encoding the variant is introduced, and the microorganism may have a significantly increased ability to produce L-branched-chain amino acids compared to a wild-type microorganism, a microorganism containing a natural-type acetohydroxy acid synthase protein, a non-modified microorganism containing a acetohydroxy acid synthase protein, and a microorganism not containing a acetohydroxy acid synthase protein.

Still another aspect of the present disclosure provides a method for producing L-branched-chain amino acids, which includes: culturing a microorganism producing L-branched-chain amino acids; and recovering the L-branched-chain amino acids from the microorganism or cultured medium in the above step.

As used herein, the term "culture" refers to culturing of a microorganism under artificially controlled environmental conditions. In the present disclosure, the method for producing an L-branched-chain amino acid using a microorganism capable of producing an L-branched-chain amino acid may be carried out by a method widely known in the art. Specifically, the culture may be carried out in a batch process, fed-batch process, or repeated fed-batch process, but the batch process is not limited thereto.

The medium used for the culture must satisfy the requirements of a particular strain used. For example, the culture medium suitable for use in culturing the *Corynebacterium* strain is known in the art (e.g., Manual of Methods for General Bacteriology by the American Society for Bacteriology, Washington D.C., USA, 1981).

Saccharide sources that can be used in the culture medium may be saccharides and carbohydrates (e.g., glucose, sucrose, lactose, fructose, maltose, starch, and cellulose); oils and lipids (e.g., soybean oil, sunflower seed oil, peanut oil, and coconut oil); fatty acids (e.g., palmitic acid, steric acid, and linoleic acid); alcohols (e.g., glycerol and ethanol);

and organic acids (e.g., acetic acid). These materials may be used independently or in combination, but the modes of use are not limited thereto.

Examples of nitrogen sources that can be used in the culture medium may include peptone, yeast extract, meat juice, malt extract, corn steep liquor, soybean meal, and urea, or inorganic compounds (e.g., ammonium sulfate, ammonium chloride, ammonium phosphate, ammonium carbonate, and ammonium nitrate). These nitrogen sources may also be used independently or in combination, but the modes of use are not limited thereto.

Phosphorous sources that can be used in the culture medium may include potassium dihydrogen phosphate, dipotassium hydrogen phosphate, or corresponding sodium-containing salts. In addition, the culture medium may contain metal salts necessary for the growth of cells. Further, in addition to the materials above, materials essential for growth (e.g., amino acids and vitamins) may be used. Additionally, precursors suitable for the culture medium may be used. The above raw materials may be adequately added into the culture during the culture process in a batch or continuous manner, but the method of addition is not limited thereto.

The pH of the culture may be adjusted using a basic compound (e.g., sodium hydroxide, potassium hydroxide, or ammonia) or an acidic compound (e.g., phosphoric acid or sulfuric acid) in an appropriate manner. Additionally, foam generation may be prevented using an anti-foaming agent (e.g., fatty acid polyglycol ester). Oxygen or oxygen-containing gas (e.g., air) may be injected into the culture so as to maintain the aerobic condition of the culture. The temperature of the culture may be generally in a range of 20° C. to 45° C., and specifically 25° C. to 40° C. Culturing may be continued until the maximum amount of the L-branched-chain amino acid is produced, and specifically for 10 to 160 hours. The L-branched-chain amino acid may be released into the culture medium or contained in the cells, but is not limited thereto.

The method of recovering an L-branched-chain amino acid from a microorganism or culture may include those well known in the art; for example, centrifugation, filtration, treatment with a protein crystallizing precipitant (salting-out method), extraction, ultrasonic disruption, ultrafiltration, dialysis, various kinds of chromatographies (e.g., molecular sieve chromatography (gel filtration), adsorption chromatography, ion-exchange chromatography, affinity chromatography, etc.), HPLC, and a combination thereof may be used, but the methods are not limited thereto. Additionally, the step of recovering the L-branched-chain amino acid may further include a purification process, and the purification process can be performed using an appropriate method known in the art.

DETAILED DESCRIPTION OF THE INVENTION

Hereinafter, the present disclosure will be described in more detail with reference to the following Examples. However, these Examples are for illustrative purposes only, and the present disclosure is not intended to be limited by these Examples.

Example 1: Preparation of Library of DNA Encoding Modified Acetohydroxy Acid Synthase Using Artificial Mutagenesis In this Example, a vector library for primary crossover-insertion within the chromosome for obtaining acetohydroxy acid synthase variants was prepared by the following method. Error-prone PCR was performed for ilvB gene (SEQ ID NO: 2) encoding acetohydroxy acid synthase (SEQ ID NO: 1) derived from *Corynebacterium glutamicum* ATCC14067, and thereby ilvB gene variants (2,395 bp) of ilvB gene variants randomly introduced with a mutation (modification) of nucleotide substitution were obtained. The error-prone PCR was performed using the GenemorphII Random Mutagenesis Kit (Stratagene), using the genomic DNA of *Corynebacterium glutamicum* ATCC14067 as a template along with primer 1 (SEQ ID NO: 3) and primer 2 (SEQ ID NO: 4).

```
primer 1 (SEQ ID NO: 3):
5'-AACCG GTATC GACAA TCCAA T-3' primer 2 (SEQ ID NO: 4):
5'-GGGTC TCTCC TTATG CCTC-3'
```

The error-prone PCR was performed such that modifications can be introduced into the amplified gene fragment at a ratio of 0 to 3.5 mutations per 1 kb of the amplified gene fragment. PCR was performed for a total of 30 cycles as follows: denaturation at 96° C. for 30 sec, annealing at 53° C. for 30 sec, and polymerization at 72° C. for 2 min.

The amplified gene fragments were connected to the pCR2.1-TOPO vector (hereinafter, "pCR2.1") using the pCR2.1-TOPO TA Cloning Kit (Invitrogen), transformed into *E. coli* DH5α, and plated on a solid LB medium containing kanamycin (25 mg/L). 20 of the transformed colonies were selected, and their nucleotide sequences were analyzed after obtaining their plasmids. As a result, it was confirmed that modifications were introduced at different locations at a frequency of 2.1 mutations/kb. Plasmids were extracted from about 20,000 transformed *E. coli* colonies, and they were named "pCR2.1-ilvB(mt) library".

Additionally, a plasmid including the wild-type ilvB gene to be used as a control was prepared. PCR was performed using the genomic DNA of *Corynebacterium glutamicum* ATCC14067 as a template along with primer 1 (SEQ ID NO: 3) and primer 2 (SEQ ID NO: 4), under the same conditions described above. For the polymerase, PfuUltra™ high-fidelity DNA polymerase (Stratagene) was used, and the prepared plasmid was named "pCR2.1-ilvB(WT)".

Example 2: Preparation of ilvB-Deficient Strain

An ilvB-deficient strain for the introduction of the pCR2.1-ilvB(mt) library was prepared using the KCCM11201P strain (KR Patent No. 10-1117022) as the parent strain.

To prepare an ilvB-deficient vector, PCR was performed using the chromosomal DNA of the wild-type *Corynebacterium glutamicum* ATCC14067 as a template and a primer set of primer 3 (SEQ ID NO: 5) and primer 4 (SEQ ID NO: 6) and a primer set of primer 5 (SEQ ID NO: 7) and primer 6 (SEQ ID NO: 8).

```
primer 3 (SEQ ID NO: 5):
5'-GCGTC TAGAG ACTTG CACGA GGAAA CG-3' primer 4 (SEQ ID NO: 6):
5'-CAGCC AAGTC CCTCA GAATT GATGT AGCAA TTATC C-3' primer 5 (SEQ ID NO: 7):
5'-GGATA ATTGC TACAT CAATT CTGAG GGACT TGGCT G-3'
```

```
-continued
primer 6 (SEQ ID NO: 8):
5'-GCGTC TAGAA CCACA GAGTC TGGAG CC-3'
```

PCR was performed as follows: denaturation at 95° C. for 5 min; 30 cycles of denaturation at 95° C. for 30 sec, annealing at 55° C. for 30 sec, and polymerization at 72° C. for 30 sec; and polymerization at 72° C. for 7 min.

As a result, a 731 bp DNA fragment (SEQ ID NO: 9), which includes the upstream region of the promoter of ilvB gene, and a 712 bp DNA fragment (SEQ ID NO: 10), which includes the 3' terminus of the ilvB gene, were obtained.

PCR was performed using the amplified DNA fragments (SEQ ID NOS: 9 and 10) and a primer set of primer 3 (SEQ ID NO: 5) and primer 6 (SEQ ID NO: 8). PCR was performed as follows: denaturation at 95° C. for 5 min; 30 cycles of denaturation at 95° C. for 30 sec, annealing at 55° C. for 30 sec, and polymerization at 72° C. for 60 sec; and polymerization at 72° C. for 7 min.

As a result, a 1,407 bp DNA fragment (SEQ ID NO: 11, hereinafter "ilvB fragment"), in which a DNA fragment including the upstream region of the promoter of ilvB gene and a DNA fragment including the 3' terminus of the ilvB gene are linked, was amplified.

The pDZ vector (KR Patent No. 10-0924065), which cannot replicate in *Corynebacterium glutamicum*, and the ilvB gene fragment amplified above were each treated with restriction enzyme XbaI, ligated using a DNA ligase, and cloned. The obtained plasmid was named "pDZ-ilvB".

The pDZ-ilvB was transformed into *Corynebacterium glutamicum* KCCM11201P by the electroporation method (*Appl. Microbiol. Biothcenol.* (1999) 52: 541-545), and the transformed strains were obtained in selection media containing kanamycin (25 mg/L) and 2 mM each of L-valine, L-leucine, and L-isoleucine. The strain, in which the gene is inactivated by the ilvB gene fragment inserted into the genome during the secondary crossover process, was obtained, and the strain was named KCCM11201PilvB.

Example 3: Preparation of Library of Modified Strains of Acetohydroxy Acid Synthase and Selection of Strains with Increased Ability of Producing L-Amino Acids The above-prepared KCCM11201PilvB strain was transformed by homologous recombination using the above-prepared pCR2.1-ilvB(mt) library, and the transformant was plated on a complex plate medium containing kanamycin (25 mg/L) and about 10,000 colonies were obtained therefrom. The colonies were named KCCM11201PilvB/pCR2.1-ilvB(mt)-1 to KCCM11201PilvB/pCR2.1-ilvB(mt)-10000.

Additionally, the above-prepared pCR2.1-ilvB(WT) vector was transformed into the KCCM11201PilvB strain to prepare a control strain and the strain was named KCCM11201PilvB/pCR2.1-ilvB(WT).

<Complex Plate Medium (pH 7.0)>

Glucose (10 g), Peptone (10 g), Beef Extract (5 g), Yeast Extract (5 g), Brain Heart Infusion (18.5 g), NaCl (2.5 g), Urea (2 g), Sorbitol (91 g), Agar (20 g) (based on 1 L of distilled water)

About 25,000 colonies obtained above were each inoculated into a selective medium (300 μL) containing the components described below and cultured in a 96-deep well plate at 32° C. at a rate of 1,000 rpm for 24 hours. The amounts of L-amino acids produced in the culture were analyzed by the ninhydrin method (*J. Biol. Chem.* 1948. 176: 367-388). Upon completion of the cultivation, 10 μL of the culture supernatant and 190 μL of a ninhydrin reaction solution were reacted at 65° C. for 30 minutes. The absorbance was measured at wavelength 570 nm using a spectrophotometer and was compared to that of the control, i.e., KCCM11201PilvB/pCR2.1-ilvB(WT), and about 213 modified strains showing an absorbance with an at least 10% increase were selected. Other colonies showed similar or reduced absorbance compared to that of the control.

<Selective Medium (pH 8.0)>

Glucose (10 g), $(NH_4)_2SO_4$ (5.5 g), $MgSO_4 \cdot 7H_2O$ (1.2 g), $KH_2PO_4$ (0.8 g), $K_2HPO_4$ (16.4 g), Biotin (100 μg), Thiamine HCl (1,000 μg), Calcium-Pantothenic Acid (2,000 μg), and Nicotinamide (2,000 μg) (based on 1 L of distilled water)

The above method was repeatedly performed for the selected 213 strains, and the top 60 kinds of strains with an improved ability of producing L-amino acids compared to that of KCCM11201PilvB/pCR2.1-ilvB(WT) were selected.

Example 4: Confirmation of L-Valine-Producing Ability of Strains Selected from the Library of Modified Strains of Acetohydroxy Acid Synthase The 60 kinds of strains selected in Example 3 were analyzed with respect to their L-valine-producing abilities after culturing them by the following method.

Each of the strains was inoculated into a 250 mL corner-baffle flask containing 25 mL of a production medium, respectively, and cultured in a shaking incubator (200 rpm) at 30° C. for 20 hours. Then, each of the 250 mL corner-baffle flasks containing 24 mL of the culture, which contained the components described below, was inoculated with 1 mL of a seed culture broth, and cultured with shaking (200 rpm) at 30° C. for 72 hours. The concentration of L-valine in each culture was analyzed by HPLC.

<Production Medium (pH 7.0)>

Glucose (100 g), $(NH_4)_2SO_4$ (40 g), Soybean Protein (2.5 g), Corn Steep Solids (5 g), Urea (3 g), $KH_2PO_4$ (1 g), $MgSO_4 \cdot 7H_2O$ (0.5 g), Biotin (100 μg), Thiamine HCl (1,000 μg), Calcium-Pantothenic Acid (2,000 μg), Nicotinamide (3,000 μg), and $CaCO_3$ (30 g) (based on 1 L of distilled water)

Among the selected 60 kinds of strains, 2 kinds of strains showing an increase in L-valine concentration were selected, and the cultivation and analysis were performed repeatedly. The analysis results of the L-valine concentration are shown in Table 1 below. The remaining 58 kinds of strains actually showed a decrease in L-valine concentration.

TABLE 1

Concentration of L-Valine Produced by Two Selected Strains of KCCM11201PilvB/pCR2.1-ilvB(mt)

| | | L-Valine (g/L) | | | |
|---|---|---|---|---|---|
| | Strain | Batch 1 | Batch 2 | Batch 3 | Mean |
| Control | KCCM11201PilvB/pCR2.1-ilvB(WT) | 2.7 | 2.9 | 2.9 | 2.8 |
| 1 | KCCM11201PilvB/pCR2.1-ilvB(mt)-5602 | 3.1 | 3.5 | 3.4 | 3.3 |
| 2 | KCCM11201PilvB/pCR2.1-ilvB(mt)-7131 | 2.9 | 3.3 | 3.1 | 3.1 |

As a result of the analysis of the L-valine concentration of the 2 selected strains, it was confirmed that the L-valine yield of the two strains was increased by 20.7% at maximum compared to that of the control strain, KCCM11201PilvB/pCR2.1-ilvB(WT).

Example 5: Confirmation of ilvB Gene Modification in Strains Selected from a Library of Modified Strains of Acetohydroxy Acid Synthase To confirm the random modifications introduced into the acetohydroxy acid synthase of the 2 selected strains in Example 4, the nucleotide sequences of ilvB gene were analyzed. For determining the nucleotide sequences, PCR was performed using a primer set of primer 7 (SEQ ID NO: 12) and primer 8 (SEQ ID NO: 13).

```
primer 7 (SEQ ID NO: 12):
5'-CGCTT GATAA TACGC ATG-3' primer 8 (SEQ ID NO: 13):
5'-GAACA TACCT GATAC GCG-3'
```

The obtained modified ilvB gene fragments were each subjected to nucleotide sequence analysis, and the results were compared to the nucleotide sequence of wild-type ilvB gene (i.e., SEQ ID NO: 2). As a result, the nucleotide sequences of modified ilvB gene were confirmed, and the amino acid sequences of modified acetohydroxy acid synthase proteins were confirmed. The information of the selected two kinds of modified acetohydroxy acid synthase proteins is shown in Table 2 below.

TABLE 2

Information of Selected Two Kinds of Modified Acetohydroxy Acid Synthase Proteins of KCCM11201P/pCR2.1-ilvB(mt)

| Strain | Amino Acid Modification of Acetohydroxy Acid Synthase |
| --- | --- |
| KCCM11201PilvB/pCR2.1-ilvB(mt)-5602 | W503Q |
| KCCM11201PilvB/pCR2.1-ilvB(mt)-7131 | T96S |

Example 6: Preparation of Vector for Introducing Modification in Acetohydroxy Acid Synthase To confirm the effects of the modified acetohydroxy acid synthase proteins which were confirmed in Example 5, a vector capable of introducing the modified acetohydroxy acid synthase proteins onto the chromosome was prepared.

Based on the confirmed nucleotide sequences, a primer set of the primer 9 (SEQ ID NO: 14) and the primer 10 (SEQ ID NO: 15) and a primer set of the primer 11 (SEQ ID NO: 16) and the primer 12 (SEQ ID NO: 17), in which an XbaI restriction site was inserted at the 5' end, were synthesized. Then, PCR was performed using each of the selected two kinds of chromosomal DNAs as a template using these primer sets, and thereby the modified ilvB gene fragments were amplified. PCR was performed as follows: denaturation at 94° C. for 5 min; 30 cycles of denaturation at 94° C. for 30 sec, annealing at 56° C. for 30 sec, and polymerization at 72° C. for 2 min; and polymerization at 72° C. for 7 min.

```
primer 9 (SEQ ID NO: 14):
5'-CGCTC TAGAC AAGCA GGTTG AGGTT CC-3' primer 10 (SEQ ID NO: 15):
5'-CGCTC TAGAC ACGAG GTTGA ATGCG CG-3' primer 11 (SEQ ID NO: 16):
5'-CGCTC TAGAC CCTCG ACAAC ACTCA CC-3' primer 12 (SEQ ID NO: 17):
5'-CGCTC TAGAT GCCAT CAAGG TGGTG AC-3'
```

The two kinds of gene fragments amplified by PCR were treated with XbaI to obtain the respective DNA fragments, and linked these fragments to the pDZ vector for chromosomal introduction, which includes an XbaI restriction site therein, transformed into *E. coli* DH5α, and the transformants were spread on an LB solid medium containing kanamycin (25 mg/L).

The colonies transformed with a vector inserted with a target gene were selected by PCR, and the plasmids were obtained by a commonly known plasmid extraction method. These plasmids were named pDZ-ilvB(W503Q) and pDZ-ilvB(T96S), each according to the modifications inserted into the ilvB gene.

Example 7: Preparation of KCCM11201P-Derived Strains with Modification in Acetohydroxy Acid Synthase and Comparison of their L-Valine-Producing Abilities The two kinds of vectors introduced with novel modifications prepared in Example 6 were each transformed into the *Corynebacterium glutamicum* KCCM11201P, which is a strain producing L-valine, by a two-step homologous chromosome recombination. Then, the strains introduced with the ilvB gene modification on the chromosome were selected by the analysis of nucleotide sequences. The strains introduced with the ilvB gene modification were named KCCM11201P::ilvB(W503Q) and KCCM11201P::ilvB(T96S). Additionally, the pDZ-ilvB(T96S) vector, between the vectors introduced with the above modification, was transformed into the KCCM11201P::ilvB(W503Q) strain prepared above. Then, the strains into which the two kinds of modifications on the chromosome were introduced were named KCCM11201P::ilvB(W503Q/T96S).

The strains were cultured in the same manner as in Example 4, and the L-valine concentrations were analyzed from the cultured strains (Table 3).

TABLE 3

Concentration of L-Valine Produced by KCCM11201P-Derived Strains Introduced with Modified Acetohydroxy Acid Synthase (g/L)

| | Strain | Batch 1 | Batch 2 | Batch 3 | Mean |
| --- | --- | --- | --- | --- | --- |
| Control | KCCM11201P | 2.9 | 2.8 | 2.8 | 2.8 |
| 1 | KCCM11201P::ilvB (W503Q) | 3.3 | 3.2 | 3.3 | 3.3 |
| 2 | KCCM11201P::ilvB (T96S) | 3.2 | 3.0 | 3.1 | 3.1 |
| 3 | KCCM11201P::ilvB (W503Q/T96S) | 3.3 | 3.4 | 3.4 | 3.4 |

As a result, two novel strains introduced with modifications (KCCM11201P::ilvB(W503Q) and KCCM11201P::ilvB(T96S)) showed a maximum increase of 17.8% in L-valine-producing ability compared to the parent strain, and the strain introduced with both modifications (KCCM11201P::ilvB(W503Q/T96S) showed an increase of 21.4% in L-valine-producing ability compared to the parent strain.

Accordingly, considering that acetohydroxy acid synthase is the first enzyme in the biosynthesis pathways of L-branched-chain amino acids, the acetohydroxy acid synthase large subunit variants of the present disclosure are expected to have an effect on the production increase of L-isoleucine and L-leucine as well as L-valine.

The present inventors have named the strains with an improved ability of L-valine production (i.e., KCCM11201P::ilvB(W503Q) and KCCM11201P::ilvB (T96S)) as *Corynebacterium glutamicum* KCJ-0793 and *Corynebacterium glutamicum* KCJ-0796, and deposited them with the Korean Culture Center of Microorganisms (KCCM) on Jan. 25, 2016, under the Accession Numbers KCCM11809P and KCCM11810P.

Example 8: Preparation of Overexpression Vector for L-Valine Biosynthesis Containing DNA Encoding Modified Acetohydroxy Acid Synthase As a control group, an overexpression vector for L-valine biosynthesis was prepared from *Corynebacterium glutamicum* KCCM11201P, which is a strain producing L-valine. Additionally, overexpression vectors for L-valine biosynthesis, in which DNAs encoding acetohydroxy acid synthase modified from each of KCCM11201P::ilvB(W503Q) and KCCM11201P::ilvB(T96S) prepared in Example 7 are included, were prepared.

For the preparation of the above vectors, the primer 13 (SEQ ID NO: 18), in which a BamHI restriction site was inserted at the 5' end, and the primer 14 (SEQ ID NO: 19), in which an XbaI restriction site was inserted at the 3' end, were synthesized. Using the primer set, PCR was performed using each of the chromosomal DNAs of *Corynebacterium glutamicum* KCCM11201P (i.e., a strain producing L-valine) and the strains prepared in Example 7 (i.e., KCCM11201P::ilvB(W503Q) and KCCM11201P::ilvB (T96S)) as a template, and thereby two kinds of modified ilvBN gene fragments were amplified. PCR was performed as follows: denaturation at 94° C. for 5 min; 30 cycles of denaturation at 94° C. for 30 sec, annealing at 56° C. for 30 sec, and polymerization at 72° C. for 4 min; and polymerization at 72° C. for 7 min.

```
primer 13 (SEQ ID NO: 18):
5'-CGAGG ATCCA ACCGG TATCG ACAAT CCAAT-3' primer 14 (SEQ ID NO: 19):
5'-CTGTC TAGAA ATCGT GGGAG TTAAA CTCGC-3'
```

The two kinds of gene fragments amplified by PCR were treated with BamHI and XbaI to obtain their respective DNA fragments. These DNA fragments were linked to the pECCG117 overexpression vector having BamHI and XbaI restriction sites, transformed into *E. coli* DH5α, and plated on a solid LB medium containing kanamycin (25 mg/L).

The colonies transformed with a vector inserted with a target gene were selected by PCR and the plasmids were obtained by a commonly known plasmid extraction method. These plasmid were named pECCG117-ilvBN, pECCG117-ilvB(W503Q)N, and pECCG117-ilvB(T96S)N, each according to the modifications inserted into the ilvB gene.

Example 9: Preparation of Overexpression Vector for L-Valine Biosynthesis Containing DNA Encoding Modified Acetohydroxy Acid Synthase in which an Amino Acid is Substituted with Another Amino Acid at the Same Position In the modified acetohydroxy acid synthase proteins confirmed in Example 5, to confirm the effects of position in modification, vectors were prepared in which the 96$^{th}$ amino acid is substituted with an amino acid other than threonine or serine, and the 503$^{rd}$ amino acid is substituted with an amino acid other than tryptophan or glutamine.

Specifically, overexpression vectors for L-valine biosynthesis, in which a modification where the 503$^{rd}$ amino acid of acetohydroxy acid synthase is substituted with asparagine or leucine or a modification where the 96$^{th}$ amino acid is substituted with alanine or cysteine, were prepared from *Corynebacterium glutamicum* KCCM11201P, which is a strain producing L-valine. The substituted amino acids are only examples of representative amino acids that can be substituted, and the amino acids are not limited thereto.

For the preparation of these vectors, first, PCR was performed using the chromosomal DNA of *Corynebacterium glutamicum* KCCM11201P as a template and a primer set of the primer 13 (SEQ ID NO: 18) and the primer 15 (SEQ ID NO: 20) and a primer set of the primer 16 (SEQ ID NO: 21) and the primer 14 (SEQ ID NO: 19), and thereby an about 2,041 bp DNA fragment having a BamHI restriction site at the 5' end and a 1,055 bp DNA fragment having an XbaI restriction site at the 3' end were amplified. PCR was performed as follows: denaturation at 94° C. for 5 min; 30 cycles of denaturation at 94° C. for 30 sec, annealing at 56° C. for 30 sec, and polymerization at 72° C. for 2 min; and polymerization at 72° C. for 7 min.

```
primer 15 (SEQ ID NO: 20):
5'-CTTCA TAGAA TAGGG TCTGG TTTTG GCGAA CCATG
CCCAG-3' primer 16 (SEQ ID NO: 21):
5'-CTGGG CATGG TTCGC CAAAA CCAGA CCCTA TTCTA
TGAAG-3'
```

Then, PCR was performed using the two amplified DNA fragments as a template and a primer set of the primer 13 (SEQ ID NO: 18) and the primer 14 (SEQ ID NO: 19). PCR was performed as follows: denaturation at 94° C. for 5 min; 30 cycles of denaturation at 94° C. for 30 sec, annealing at 56° C. for 30 sec, and polymerization at 72° C. for 4 min; and polymerization at 72° C. for 7 min.

As a result, an ilvBN gene fragment in which a modification where the 503$^{rd}$ amino acid of acetohydroxy acid synthase is substituted with asparagine was obtained.

In the same manner, PCR was performed using the chromosomal DNA of *Corynebacterium glutamicum* KCCM11201P as a template and a primer set of the primer 13 (SEQ ID NO: 18) and the primer 17 (SEQ ID NO: 22) and a primer set of the primer 18 (SEQ ID NO: 23) and the primer 14 (SEQ ID NO: 19), and thereby an about 2,041 bp DNA fragment having a BamHI restriction site at the 5' end and a 1,055 bp DNA fragment having an XbaI restriction site at the 3' end were amplified.

```
primer 17 (SEQ ID NO: 22):
5'-CTTCA TAGAA TAGGG TCTGC AGTTG GCGAA CCATG
CCCAG-3'
```

-continued primer 18 (SEQ ID NO: 23):
5'-CTGGG CATGG TTCGC CAACT GCAGA CCCTA TTCTA
TGAAG-3'

Then, PCR was performed using the two amplified DNA fragments as a template and a primer set of the primer 13 (SEQ ID NO: 18) and the primer 14 (SEQ ID NO: 19).

As a result, an ilvBN gene fragment in which a modification where the 503$^{rd}$ amino acid of acetohydroxy acid synthase is substituted with leucine was obtained.

In the same manner, PCR was performed using the chromosomal DNA of *Corynebacterium glutamicum* KCCM11201P as a template and a primer set of the primer 13 (SEQ ID NO: 18) and the primer 19 (SEQ ID NO: 24) and a primer set of the primer 20 (SEQ ID NO: 25) and the primer 14 (SEQ ID NO: 19), and thereby an about 819 bp DNA fragment having a BamHI restriction site at the 5' end and a 2,276 bp DNA fragment having an XbaI restriction site at the 3' end were amplified.

primer 19 (SEQ ID NO: 24):
5'-GGTTG CGCCT GGGCC AGATG CTGCA ATGCA GACGC
CAAC-3' primer 20 (SEQ ID NO: 25):
5'-GTTGG CGTCT GCATT GCAGC ATCTG GCCCA GGCGC
AACC-3'

Then, PCR was performed using the two amplified DNA fragments as a template and a primer set of the primer 13 (SEQ ID NO: 18) and the primer 14 (SEQ ID NO: 19).

As a result, an ilvBN gene fragment in which a modification where the 96$^{th}$ amino acid of acetohydroxy acid synthase is substituted with alanine was obtained.

In the same manner, PCR was performed using the chromosomal DNA of *Corynebacterium glutamicum* KCCM11201P as a template and a primer set of the primer 13 (SEQ ID NO: 18) and the primer 21 (SEQ ID NO: 26) and a primer set of the primer 22 (SEQ ID NO: 27) and the primer 14 (SEQ ID NO: 19), and thereby an about 819 bp DNA fragment having a BamHI restriction site at the 5' end and a 2,276 bp DNA fragment having an XbaI restriction site at the 3' end were amplified.

primer 21 (SEQ ID NO: 26):
5'-GGTTG CGCCT GGGCC AGAGC ATGCA ATGCA GACGC
CAAC-3' primer 22 (SEQ ID NO: 27):
5'-GTTGG CGTCT GCATT GCATG CTCTG GCCCA GGCGC
AACC-3'

Then, PCR was performed using the two amplified DNA fragments as a template and a primer set of the primer 13 (SEQ ID NO: 18) and the primer 14 (SEQ ID NO: 19).

As a result, an ilvBN gene fragment in which a modification where the 96$^{th}$ amino acid of acetohydroxy acid synthase is substituted with cysteine was obtained.

Using the same method as in Example 8, the four kinds PCR-amplified modified gene fragments were treated with restriction enzymes BamHI and XbaI, and thereby the respective DNA fragments were obtained. These DNA fragments were each linked to the overexpression vector pECCG117 having BamHI and XbaI restriction sites, transformed into *E. coli* DH5a, and plated on a solid LB medium containing kanamycin (25 mg/L).

The colonies transformed with a vector inserted with a target gene were selected by PCR, and the plasmids were obtained by a commonly known plasmid extraction method. These plasmid were each named pECCG117-ilvB(W503N) N, pECCG117-ilvB(W503L)N, pECCG117-ilvB(T96A)N, and pECCG117-ilvB(T96C)N, each according to the sequence of modifications inserted into the ilvB gene.

Example 10: Preparation of Strains in which Wild-Type-Derived Modified Acetohydroxy Acid Synthase is Introduced and Comparison of L-Valine-Producing Abilities The overexpression vectors for L-valine biosynthesis prepared in Examples 8 and 9 (i.e., pECCG117-ilvBN, pECCG117-ilvB(W503Q)N, pECCG117-ilvB(T96S)N and pECCG117-ilvB(W503N)N, pECCG117-ilvB(W503L)N, pECCG117-ilvB(T96A)N, and pECCG117-ilvB(T96C)N) were each inserted into the wild-type *Corynebacterium glutamicum* strain (ATCC13032) by electroporation. The prepared strains were each named *Corynebacterium glutamicum* ATCC13032::pECCG117-ilvBN, *Corynebacterium glutamicum* ATCC13032::pECCG117-ilvB (W503 Q)N, *Corynebacterium glutamicum* ATCC13032::pECCG117-ilvB(T96S)N, *Corynebacterium glutamicum* ATCC13032:: pECCG117-ilvB(W503N)N, *Corynebacterium glutamicum* ATCC13032::pECCG117-ilvB(W503L)N, *Corynebacterium glutamicum* ATCC13032::pECCG117-ilvB(T96A)N, and *Corynebacterium glutamicum* ATCC13032:: pECCG117-ilvB(T96C)N.

Since those strains which are transformed with these vectors will be provided with kanamycin resistance, the presence of transformation was confirmed by checking the growth of these strains in a medium containing kanamycin at a concentration of 25 mg/L.

Each of the strains was inoculated into a 250 mL corner-baffle flask containing 25 mL of the production medium and cultured with shaking at 200 rpm at 30° C. for 72 hours. The concentration of L-valine in each culture was analyzed by HPLC (Table 4).

TABLE 4

Concentration of L-valine Production by Strains in Which Wild-Type-Derived Modified Acetohydroxy Acid Synthase is Introduced

| | | L-Valine (g/L) | | | |
| --- | --- | --- | --- | --- | --- |
| | Strain | Batch 1 | Batch 2 | Batch 3 | Mean |
| Control | ATCC13032::pECCG117-ilvBN | 0.1 | 0.1 | 0 | 0.1 |
| 1 | ATCC13032::pECCG117-ilvB(W503Q)N | 0.8 | 0.8 | 0.7 | 0.8 |
| 2 | ATCC13032::pECCG117-ilvB(T96S)N | 0.4 | 0.5 | 0.5 | 0.5 |

TABLE 4-continued

Concentration of L-valine Production by Strains in Which Wild-Type-Derived Modified Acetohydroxy Acid Synthase is Introduced

|   | Strain | L-Valine (g/L) | | | |
|---|---|---|---|---|---|
|   |   | Batch 1 | Batch 2 | Batch 3 | Mean |
| 3 | ATCC13032::pECCG117-ilvB(W503N)N | 0.7 | 0.6 | 0.5 | 0.6 |
| 4 | ATCC13032::pECCG117-ilvB(W503L)N | 0.7 | 0.7 | 0.5 | 0.5 |
| 5 | ATCC13032::pECCG117-ilvB(T96A)N | 0.2 | 0.3 | 0.2 | 0.2 |
| 6 | ATCC13032::pECCG117-ilvB(T96C)N | 0.4 | 0.3 | 0.5 | 0.4 |

As a result, it was confirmed that the novel modifications in which the $96^{th}$ or $503^{rd}$ amino acid of acetohydroxy acid synthase is substituted with another amino acid showed a maximum increase of 700% in the L-valine-producing ability compared to the control group. This result confirmed the importance of the $96^{th}$ and $503^{rd}$ amino acid positions of acetohydroxy acid synthase, and these amino acid positions are expected to affect the ability of producing other branched-chain amino acids as well as L-valine.

Example 11: Preparation of Strains in which Modified Acetohydroxy Acid Synthase is Introduced and Comparison of L-Valine-Producing Abilities To confirm whether the acetohydroxy acid synthase large subunit variants of the present disclosure have an influence on the increase in the ability of producing other L-branched-chain amino acids, as another embodiment of the L-branched-chain amino acids, the ability of producing L-leucine was examined.

Specifically, the two vectors in which novel modifications were introduced prepared in Example 6 were each transformed by a two-step homologous recombination into the *Corynebacterium glutamicum* KCCM11661P (Korean Patent Application No. 10-2015-0119785 and Korean Patent Application Publication No. 10-2017-0024653), which is an L-leucine-producing strain. Then, the strains in which the ilvB gene modification is introduced on the chromosome thereof were selected by nucleotide sequence analysis, and the strains in which the ilvB gene modification is introduced were named KCCM11661P::ilvB(W503Q) and KCCM11661P::ilvB(T96S).

The *Corynebacterium glutamicum* KCCM11661P having resistance to norleucine (NL) is a mutant strain derived from *Corynebacterium glutamicum* ATCC 14067 and was obtained as follows.

Specifically, the *Corynebacterium glutamicum* ATCC 14067 was cultured in an activation medium for 16 hours, and the activated strain was inoculated into a seed medium, which was sterilized at 121° C. for 5 minutes, and cultured for 14 hours, and 5 mL of the culture was recovered. The recovered culture was washed with 100 mM citric acid buffer and N-methyl-N'-nitro-N-nitrosoguanidine (NTG) was added thereto to a final concentration of 200 mg/L and treated for 20 minutes, and washed with 100 mM phosphate buffer. The strains treated with NTG were plated on a minimal medium and the death rate was calculated, and as a result, the death rate was shown to be 85%.

To obtain a mutant strain having resistance to norleucine (NL), the NTG-treated strains were plated on a minimal medium containing NL at a final concentration of 20 mM, 30 mM, 40 mM, and 50 mM, respectively. Then, the strains were cultured at 30° C. for 5 days, and thereby an NL-resistant mutant strain was obtained.

<Activation Medium>
Meat Juice (1%), Polypeptone (1%), NaCl (0.5%), Yeast Extract (1%), Agar (2%), pH 7.2

<Seed Medium>
Glucose (5%), Bactopeptone (1%), NaCl (0.25%), Yeast Extract (1%), Urea (0.4%), pH 7.2

<Minimal Medium>
Glucose (1%), Ammonium Sulfate (0.4%), Magnesium Sulfate (0.04%), Monopotassium Phosphate (0.1%), Urea (0.1%), Thiamine (0.001%), Biotin (200 µg/L), Agar (2%), pH 7.0

The thus-obtained mutant strain was named *Corynebacterium glutamicum* KCJ-24 and deposited at the Korean Culture Center of Microorganisms (KCCM), which is recognized as an international depositary authority under the Budapest Treaty, on Jan. 22, 2015, under the Accession Number KCCM11661P.

The KCCM11661P::ilvB(W503Q) and KCCM11661P::ilvB(T96S) were cultured in the same manner as in Example 4, and the L-leucine concentration in each culture therefrom was analyzed (Table 5).

TABLE 5

Concentration of L-Leucine Production by Strains in Which KCCM11661P-Dervied Modified Acetohydroxy Acid Synthase is Introduced (g/L)

|   | Strain | Batch 1 | Batch 2 | Batch 3 | Mean |
|---|---|---|---|---|---|
| Control | KCCM11661P | 2.7 | 2.6 | 2.9 | 2.7 |
| 1 | KCCM11661P::ilvB(W503Q) | 3.1 | 3.3 | 3.3 | 3.2 |
| 2 | KCCM11661PP::ilvB(T96S) | 3.0 | 3.2 | 3.1 | 3.1 |

The two strains in which novel modifications were introduced (i.e., KCCM11661P::ilvB(W503Q) and KCCM11661P::ilvB(T96S)) showed a maximum increase of 26.9% in the L-leucine-producing ability compared to their parent strain.

Example 12: Preparation of Strains in which KCCM11662P-Derived Modified Acetohydroxy Acid Synthase is Introduced and Comparison of L-Leucine-Producing Abilities The two vectors in which novel modifications were introduced prepared in Example 6 were each transformed by a two-step homologous recombination into the *Corynebacterium glutamicum* KCCM11662P (Korean Patent Application No. 10-2015-0119785 and Korean Patent Application Publication No. 10-2017-0024653), which is an L-leucine-producing strain. Then, the strains in which the ilvB gene modification is introduced on the chromosome thereof were selected by nucleotide sequence analysis, and the strains in which the ilvB gene modification is introduced were named KCCM11662P::ilvB(W503Q) and KCCM11662P::ilvB (T96S).

The *Corynebacterium glutamicum* KCCM11662P having resistance to norleucine (NL) is a mutant strain derived from *Corynebacterium glutamicum* ATCC 13869 and was obtained as follows.

Specifically, using *Corynebacterium glutamicum* ATCC 13869 as the parent strain, the strain was cultured in the same manner for obtaining the KCCM11662P of Example 11 and finally an NL-resistant mutant strain was obtained.

The thus-obtained mutant strain was named *Corynebacterium glutamicum* KCJ-28 and deposited at the Korean Culture Center of Microorganisms (KCCM), which is recognized as an international depositary authority under the Budapest Treaty, on Jan. 22, 2015, under the Accession Number KCCM11662P.

The KCCM11662P::ilvB(W503Q) and KCCM11662P::ilvB(T96S) were cultured in the same manner as in Example 4, and the L-leucine concentration in each culture therefrom was analyzed (Table 6).

TABLE 6

Concentration of L-Leucine Production by Strains in Which KCCM11662P-Dervied Modified Acetohydroxy Acid Synthase is Introduced (g/L)

|  | Strain | Batch 1 | Batch 2 | Batch 3 | Mean |
|---|---|---|---|---|---|
| Control | KCCM11662P | 3.1 | 3.0 | 3.1 | 3.1 |
| 1 | KCCM11662P::ilvB(W503Q) | 3.5 | 3.4 | 3.3 | 3.4 |
| 2 | KCCM11662PP::ilvB(T96S) | 3.3 | 3.3 | 3.2 | 3.3 |

The two strains in which novel modifications were introduced (i.e., KCCM11662P::ilvB(W503Q) and KCCM11662P::ilvB(T96S)) showed a maximum increase of 13.3% in the L-leucine-producing ability compared to their parent strain.

From the foregoing, a skilled person in the art to which the present disclosure pertains will be able to understand that the present disclosure may be embodied in other specific forms without modifying the technical concepts or essential characteristics of the present disclosure. In this regard, the exemplary embodiments disclosed herein are only for illustrative purposes and should not be construed as limiting the scope of the present disclosure. On the contrary, the present disclosure is intended to cover not only the exemplary embodiments but also various alternatives, modifications, equivalents, and other embodiments that may be included within the spirit and scope of the present disclosure as defined by the appended claims.

The invention claimed is:

1. A polynucleotide encoding an acetohydroxy acid synthase variant having acetohydroxy acid synthase activity, wherein the acetohydroxy acid synthase variant comprises an acetohydroxy acid synthase large subunit (acetolactate synthase large subunit; IlvB protein) having at least 95% sequence identity with the polypeptide of SEQ ID NO: 1, wherein said large subunit comprises a substitution at the position corresponding to position 96 of the polypeptide of SEQ ID NO: 1, and wherein the amino acid at the position corresponding to position 96 of the polypeptide of SEQ ID NO: 1 is a serine, cysteine, or alanine.

2. The polynucleotide according to claim 1, wherein the acetohydroxy acid synthase large subunit further comprises a substitution at the position corresponding to position 503 of the polypeptide of SEQ ID NO:1, and wherein the amino acid at the position corresponding to position 503 of the polypeptide of SEQ ID NO:1 is a glutamine.

3. A microorganism of the genus *Corynebacterium* producing an L-branched-chain amino acid,
wherein the microorganism comprises an acetohydroxy acid synthase variant or a polynucleotide encoding the acetohydroxy acid synthase variant,
wherein the acetohydroxy acid synthase variant comprises an acetohydroxy acid synthase large subunit (acetolactate synthase large subunit; IlvB protein) having at least 95% sequence identity with the polypeptide of SEQ ID NO: 1,
wherein said large subunit comprises a substitution at the position corresponding to position 96 of the polypeptide of SEQ ID NO: 1, and
wherein the amino acid at the position corresponding to position 96 of the polypeptide of SEQ ID NO: 1 is a serine, cysteine, or alanine.

4. The microorganism according to claim 3, wherein the acetohydroxy acid synthase large subunit further comprises a substitution at the position corresponding to position 503 of the polypeptide of SEQ ID NO:1, and wherein the amino acid at the position corresponding to position 503 of the polypeptide of SEQ ID NO:1 is a glutamine.

5. The microorganism according to claim 3, wherein the microorganism of the genus *Corynebacterium* is *Corynebacterium glutamicum*.

6. The microorganism according to claim 3, wherein the L-branched-chain amino acid is L-valine or L-leucine.

* * * * *

SEQUENCE LISTING

```
<160> NUMBER OF SEQ ID NOS: 39

<210> SEQ ID NO 1
<211> LENGTH: 626
<212> TYPE: PRT
<213> ORGANISM: Artificial Sequence
<220> FEATURE:
<223> OTHER INFORMATION: acetohydroxy acid synthase

<400> SEQUENCE: 1

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Gln Ala Ile
                20                  25                  30

Val Arg Ser Leu Glu Glu Leu Asn Ala Asp Ile Val Phe Gly Ile Pro
            35                  40                  45

Gly Gly Ala Val Leu Pro Val Tyr Asp Pro Leu Tyr Ser Ser Thr Lys
        50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asp Pro Asn Asp Ile
145                 150                 155                 160
```

```
Pro Gln Ala Leu Ala Glu Ala Phe His Leu Ala Ile Thr Gly Arg Pro
            165                 170                 175

Gly Pro Val Leu Val Asp Ile Pro Lys Asp Val Gln Asn Ala Glu Leu
            180                 185                 190

Asp Phe Val Trp Pro Lys Ile Asp Leu Pro Gly Tyr Arg Pro Val
            195                 200                 205

Ser Thr Pro His Ala Arg Gln Ile Glu Gln Ala Val Lys Leu Ile Gly
            210                 215                 220

Glu Ala Lys Lys Pro Val Leu Tyr Ile Gly Gly Val Ile Lys Ala
225                 230                 235                 240

Asp Ala His Glu Glu Leu Arg Ala Phe Ala Glu Tyr Thr Gly Ile Pro
            245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
            275                 280                 285

Ala Leu Gln Arg Ser Asp Leu Leu Ile Ala Ile Gly Ser Arg Phe Asp
            290                 295                 300

Asp Arg Val Thr Gly Asp Val Asp Thr Phe Ala Pro Ala Lys Ile
305                 310                 315                 320

Ile His Ala Asp Ile Asp Pro Ala Glu Ile Gly Lys Ile Lys Gln Val
            325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
            370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
            405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
            435                 440                 445

Ala Leu Gly Ala Lys Ala Gly Ala Pro Asp Lys Glu Val Trp Ala Ile
            450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
            485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
            515                 520                 525

Thr Leu Ser Glu Gly Leu Gly Cys Val Ala Ile Arg Val Thr Lys Ala
            530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
            565                 570                 575
```

```
Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
    610                 615                 620

Glu Ala
625

<210> SEQ ID NO 2
<211> LENGTH: 1881
<212> TYPE: DNA
<213> ORGANISM: Artificial Sequence
<220> FEATURE:
<223> OTHER INFORMATION: acetohydroxy acid synthase

<400> SEQUENCE: 2
gtgaatgtgg cagcttctca acagcccact cccgccacgg ttgcaagccg tggtcgatcc      60
gccgcccctg agcggatgac aggtgcacag gcaattgttc gatcgctcga ggagcttaac     120
gccgacatcg tgttcggtat tcctggtggt gcggtgctac cggtgtatga cccgctctat     180
tcctccacaa aggtgcgcca cgtcctggtg cgccacgagc agggcgcagg ccacgcagca     240
accggctacg cgcaggttac tggacgcgtt ggcgtctgca ttgcaacctc tggcccaggc     300
gcaaccaact tggttacccc aatcgctgat gcaaacttgg actccgttcc catggttgcc     360
atcaccggcc aggtcggaag tggcctgctg gtaccgatgc tttccaggaa gccgatatc     420 cgcggcatca ccatgccagt gaccaagcac aacttcatgg tcaccgaccc caacgacatt     480
ccacaggcat tggctgaggc attccacctc gcgattactg tcgccctggc cctgttctg     540 gtggatattc ctaaggatgt ccaaaacgct gaattggatt cgtctggcc accaaagatc     600 gacctgccag gctaccgccc agtttctact ccgcatgctc gacagattga gcaggctgtc     660
aaactgatcg tgaagccaa aaagccagtc ctttacattg gcggcggcgt tatcaaggct     720
gatgcacacg aagaactgcg tgcatttgct gagtacaccg gcatcccagt tgtcaccacc     780
ttgatggcat gggtacctt cccagagtcc cacgagctgc acatgggtat gccaggcatg     840
cacggcaccg tgtccgctgt tggcgcactg cagcgcagtg acctgctgat tgctatcggt     900
tcccgcttcg acgaccgcgt caccggtgac gttgacacct cgcacctga tgccaagatc     960 attcacgctg acattgatcc tgccgaaatc ggcaagatca gcaggttga ggttccaatc    1020 gtgggcgatg cccgcgaggt tcttgctcgt ctgctggaaa ccaccaaggc aagcaaggca    1080
gagaccgagg acatctccga gtgggttgat tacctcaagg gcctcaaggc acgttcccca    1140
cgtggctacg acgagcagcc aggcgatctg ctggcaccac agtttgtcat tgaaaccctg    1200
tccaaggaag ttggccccga cgcaatttac tgcgccggcg ttggccagca ccagatgtgg    1260
gcagctcagt tcgttgactt tgaaaagcca cgcacctggc tcaactctgg cggcctgggc    1320
accatgggct acgcagttcc tgcggctctt ggagcaaagg ctggcgcacc tgacaaggaa    1380
gtctgggcta cgacggcga cggctgtttc cagatgacca accaggaact caccaccgcc    1440
gcagttgaag gtttcccat taagatcgca ctaatcaaca cgaaaacct gggcatggtt    1500 cgccaatggc agaccctatt ctatgaagga cggtactcaa atactaaact tcgtaaccag    1560
ggcgagtaca tgcccgactt tgttacccct tctgagggac ttggctgtgt tgccatccgc    1620
gtcaccaaag cggaggaagt actgccagcc atccaaaagg ctcagagat caacgaccgc    1680 ccagtagtca tcgacttcat cgtcggtgaa gacgcacagg tatggccaat ggtgtctgct    1740
```

```
ggatcatcca actccgatat ccagtacgca ctcggattgc gcccattctt tgatggtgat    1800
gaatctgcag cagaagatcc tgccgacatt cacgaagccg tcagcgacat tgatgccgcc    1860
gttgaatcga ccgaggcata a                                              1881
```

<210> SEQ ID NO 3
<211> LENGTH: 21
<212> TYPE: DNA
<213> ORGANISM: Artificial Sequence
<220> FEATURE:
<223> OTHER INFORMATION: primer 1

<400> SEQUENCE: 3

```
aaccggtatc gacaatccaa t                                              21
```

<210> SEQ ID NO 4
<211> LENGTH: 19
<212> TYPE: DNA
<213> ORGANISM: Artificial Sequence
<220> FEATURE:
<223> OTHER INFORMATION: primer 2

<400> SEQUENCE: 4

```
gggtctctcc ttatgcctc                                                 19
```

<210> SEQ ID NO 5
<211> LENGTH: 27
<212> TYPE: DNA
<213> ORGANISM: Artificial Sequence
<220> FEATURE:
<223> OTHER INFORMATION: primer 3

<400> SEQUENCE: 5

```
gcgtctagag acttgcacga ggaaacg                                        27
```

<210> SEQ ID NO 6
<211> LENGTH: 36
<212> TYPE: DNA
<213> ORGANISM: Artificial Sequence
<220> FEATURE:
<223> OTHER INFORMATION: primer 4

<400> SEQUENCE: 6

```
cagccaagtc cctcagaatt gatgtagcaa ttatcc                              36
```

<210> SEQ ID NO 7
<211> LENGTH: 36
<212> TYPE: DNA
<213> ORGANISM: Artificial Sequence
<220> FEATURE:
<223> OTHER INFORMATION: primer 5

<400> SEQUENCE: 7

```
ggataattgc tacatcaatt ctgagggact tggctg                              36
```

<210> SEQ ID NO 8
<211> LENGTH: 27
<212> TYPE: DNA
<213> ORGANISM: Artificial Sequence
<220> FEATURE:
<223> OTHER INFORMATION: primer 6

<400> SEQUENCE: 8

```
gcgtctagaa ccacagagtc tggagcc                                        27
```

<210> SEQ ID NO 9
<211> LENGTH: 731
<212> TYPE: DNA
<213> ORGANISM: Artificial Sequence
<220> FEATURE:
<223> OTHER INFORMATION: ilvB 5' fragment

<400> SEQUENCE: 9

```
gcgtctagag acttgcacga ggaaacgcat ggtgaccatc cacggcatgc cgaccaccgt    60
tggcggtgtg acttccgtgg ctgggtgcac atcgagttca ccgaggattt ccggtgcgat   120
tttctcctgg ccaagtgcgc gacgagtcgc agcttcagag cgcgcgatga catctgtgat   180
gttttcagaa cccaacatgg ggatcggaat aacgacaacc gcacgcgacc agttattaga   240
attgttgatg cacactttcg ccgtggagtt ggggatgatc acggtctctt gtgcaatcgt   300
gcgaattttg gtcgcgcgca tggtgatctc aatgacggtg ccttcgacaa cgatgccgtt   360
gccctcaaaa cgcacccagt cacccacgcc gaattgcttt ccgtcagga tgaaaaatcc   420
ggccaagaag tccgcaacaa tcgactgcgc accaaggcca tggcagctg acgcaatggt    480
tgccggaatc gcagcgcccg cgagagagaa accaaaagcc tgcatcgcgg agacggcaag   540
catgaaaaac gccacaattt gcgcgatata acgccaacg ccagcgaacg cgagctggtt    600
cttagtggtg tccgcatcgg ctgcagactc cactcgccgc ttgataatac gcatggccag   660
tcggccgata cgtggaatca aaaacgccaa gaccaggata attgctacat caattctgag   720
ggacttggct g                                                        731
```

<210> SEQ ID NO 10
<211> LENGTH: 712
<212> TYPE: DNA
<213> ORGANISM: Artificial Sequence
<220> FEATURE:
<223> OTHER INFORMATION: ilvB 3' fragment

<400> SEQUENCE: 10

```
ggataattgc tacatcaatt ctgagggact tggctgtgtt gccatccgcg tcaccaaagc    60
ggaggaagta ctgccagcca tccaaaaggc tcgagagatc aacgaccgcc cagtagtcat   120
cgacttcatc gtcggtgaag acgcacaggt atggccaatg gtgtctgctg atcatccaa    180
ctccgatatc cagtacgcac tcggattgcg cccattcttt gatggtgatg aatctgcagc   240
agaagatcct gccgacattc acgaagccgt cagcgacatt gatgccgccg ttgaatcgac   300
cgaggcataa ggagagaccc aagatggcta attctgacgt cacccgccac atcctgtccg   360
tactcgttca ggacgtagac ggaatcattt cccgcgtatc aggtatgttc acccgacgcg   420
cattcaacct cgtgtccctc gtgtctgtaa agaccgaaac actcggcatc aaccgcatca   480
cggttgttgt cgacgccgac gagctcaaca ttgagcagat caccaagcag ctcaacaagc   540
tgatccccgt gctcaaagtc gtgcgacttg atgaagagac caccatcgcc cgcgcaatca   600
tgctggttaa ggtctctgcg gatagcacca accgtccgca gatcgtcgac gccgcgaaca   660
tcttccgcgc ccgagtcgtc gacgtggctc cagactctgt ggttctagac gc           712
```

<210> SEQ ID NO 11
<211> LENGTH: 1407
<212> TYPE: DNA
<213> ORGANISM: Artificial Sequence
<220> FEATURE:
<223> OTHER INFORMATION: ilvB 5' + 3' fragment

<400> SEQUENCE: 11

```
gcgtctagag acttgcacga ggaaacgcat ggtgaccatc cacgcatgc cgaccaccgt      60 tggcggtgtg acttccgtgg ctgggtgcac atcgagttca ccgaggattt ccggtgcgat    120
tttctcctgg ccaagtgcgc gacgagtcgc agcttcagag cgcgcgatga catctgtgat    180
gttttcagaa cccaacatgg ggatcggaat aacgacaacc gcacgcgacc agttattaga    240
attgttgatg cacactttcg ccgtggagtt ggggatgatc acggtctctt gtgcaatcgt    300
gcgaattttg gtcgcgcgca tggtgatctc aatgacggtg ccttcgacaa cgatgccgtt    360
gccctcaaaa cgcacccagt cacccacgcc gaattgcttt tccgtcagga tgaaaaatcc    420
ggccaagaag tccgcaacaa tcgactgcgc accaaggcca atggcagctg acgcaatggt    480
tgccggaatc gcagcgcccg cgagagagaa accaaaagcc tgcatcgcgg agacggcaag    540
catgaaaaac gccacaattt gcgcgatata aacgccaacg ccagcgaacg cgagctggtt    600
cttagtggtg tccgcatcgg ctgcagactc cactcgccgc ttgataatac gcatggccag    660
tcggccgata cgtggaatca aaaacgccaa gaccaggata ttgctacat caattctgag     720 ggacttggct gtgttgccat ccgcgtcacc aaagcggagg aagtactgcc agccatccaa    780
aaggctcgag agatcaacga ccgcccagta gtcatcgact tcatcgtcgg tgaagacgca    840
caggtatggc caatggtgtc tgctggatca tccaactccg atatccagta cgcactcgga    900
ttgcgcccat tctttgatgg tgatgaatct gcagcagaag atcctgccga cattcacgaa    960
gccgtcagcg acattgatgc cgccgttgaa tcgaccgagg cataaggaga gacccaagat   1020
ggctaattct gacgtcaccc gccacatcct gtccgtactc gttcaggacg tagacggaat   1080
catttcccgc gtatcaggta tgttcacccg acgcgcattc aacctcgtgt ccctcgtgtc   1140
tgtaaagacc gaaacactcg gcatcaaccg catcacggtt gttgtcgacg ccgacgagct   1200
caacattgag cagatcacca agcagctcaa caagctgatc cccgtgctca agtcgtgcg    1260 acttgatgaa gagaccacca tcgcccgcgc aatcatgctg gttaaggtct ctgcggatag   1320
caccaaccgt ccgcagatcg tcgacgccgc gaacatcttc cgcgcccgag tcgtcgacgt   1380
ggctccagac tctgtggttc tagacgc                                        1407
```

<210> SEQ ID NO 12
<211> LENGTH: 18
<212> TYPE: DNA
<213> ORGANISM: Artificial Sequence
<220> FEATURE:
<223> OTHER INFORMATION: primer 7

<400> SEQUENCE: 12

```
cgcttgataa tacgcatg                                                    18
```

<210> SEQ ID NO 13
<211> LENGTH: 18
<212> TYPE: DNA
<213> ORGANISM: Artificial Sequence
<220> FEATURE:
<223> OTHER INFORMATION: primer 8

<400> SEQUENCE: 13

```
gaacatacct gatacgcg                                                    18
```

<210> SEQ ID NO 14
<211> LENGTH: 27
<212> TYPE: DNA
<213> ORGANISM: Artificial Sequence
<220> FEATURE:

<223> OTHER INFORMATION: primer 9

<400> SEQUENCE: 14
cgctctagac aagcaggttg aggttcc                                              27

<210> SEQ ID NO 15
<211> LENGTH: 27
<212> TYPE: DNA
<213> ORGANISM: Artificial Sequence
<220> FEATURE:
<223> OTHER INFORMATION: primer 10

<400> SEQUENCE: 15
cgctctagac acgaggttga atgcgcg                                              27

<210> SEQ ID NO 16
<211> LENGTH: 27
<212> TYPE: DNA
<213> ORGANISM: Artificial Sequence
<220> FEATURE:
<223> OTHER INFORMATION: primer 11

<400> SEQUENCE: 16
cgctctagac cctcgacaac actcacc                                              27

<210> SEQ ID NO 17
<211> LENGTH: 27
<212> TYPE: DNA
<213> ORGANISM: Artificial Sequence
<220> FEATURE:
<223> OTHER INFORMATION: primer 12

<400> SEQUENCE: 17
cgctctagat gccatcaagg tggtgac                                              27

<210> SEQ ID NO 18
<211> LENGTH: 30
<212> TYPE: DNA
<213> ORGANISM: Artificial Sequence
<220> FEATURE:
<223> OTHER INFORMATION: primer 13

<400> SEQUENCE: 18
cgaggatcca accggtatcg acaatccaat                                           30

<210> SEQ ID NO 19
<211> LENGTH: 30
<212> TYPE: DNA
<213> ORGANISM: Artificial Sequence
<220> FEATURE:
<223> OTHER INFORMATION: primer 14

<400> SEQUENCE: 19
ctgtctagaa atcgtgggag ttaaactcgc                                           30

<210> SEQ ID NO 20
<211> LENGTH: 40
<212> TYPE: DNA
<213> ORGANISM: Artificial Sequence
<220> FEATURE:
<223> OTHER INFORMATION: primer 15

<400> SEQUENCE: 20
cttcatagaa tagggtctgg ttttggcgaa ccatgcccag                                40

```
<210> SEQ ID NO 21
<211> LENGTH: 40
<212> TYPE: DNA
<213> ORGANISM: Artificial Sequence
<220> FEATURE:
<223> OTHER INFORMATION: primer 16

<400> SEQUENCE: 21
ctgggcatgg ttcgccaaaa ccagacccta ttctatgaag                            40

<210> SEQ ID NO 22
<211> LENGTH: 40
<212> TYPE: DNA
<213> ORGANISM: Artificial Sequence
<220> FEATURE:
<223> OTHER INFORMATION: primer 17

<400> SEQUENCE: 22
cttcatagaa tagggtctgc agttggcgaa ccatgcccag                            40

<210> SEQ ID NO 23
<211> LENGTH: 40
<212> TYPE: DNA
<213> ORGANISM: Artificial Sequence
<220> FEATURE:
<223> OTHER INFORMATION: primer 18

<400> SEQUENCE: 23
ctgggcatgg ttcgccaact gcagacccta ttctatgaag                            40

<210> SEQ ID NO 24
<211> LENGTH: 39
<212> TYPE: DNA
<213> ORGANISM: Artificial Sequence
<220> FEATURE:
<223> OTHER INFORMATION: primer 19

<400> SEQUENCE: 24
ggttgcgcct gggccagatg ctgcaatgca gacgccaac                             39

<210> SEQ ID NO 25
<211> LENGTH: 39
<212> TYPE: DNA
<213> ORGANISM: Artificial Sequence
<220> FEATURE:
<223> OTHER INFORMATION: primer 20

<400> SEQUENCE: 25
gttggcgtct gcattgcagc atctggccca ggcgcaacc                             39

<210> SEQ ID NO 26
<211> LENGTH: 39
<212> TYPE: DNA
<213> ORGANISM: Artificial Sequence
<220> FEATURE:
<223> OTHER INFORMATION: primer 21

<400> SEQUENCE: 26
ggttgcgcct gggccagagc atgcaatgca gacgccaac                             39

<210> SEQ ID NO 27
<211> LENGTH: 39
<212> TYPE: DNA
<213> ORGANISM: Artificial Sequence
<220> FEATURE:
<223> OTHER INFORMATION: primer 22
```

```
<400> SEQUENCE: 27
gttggcgtct gcattgcatg ctctggccca ggcgcaacc                                 39

<210> SEQ ID NO 28
<211> LENGTH: 626
<212> TYPE: PRT
<213> ORGANISM: Artificial Sequence
<220> FEATURE:
<223> OTHER INFORMATION: T96S

<400> SEQUENCE: 28
```

| Met | Asn | Val | Ala | Ala | Ser | Gln | Gln | Pro | Thr | Pro | Ala | Thr | Val | Ala | Ser |
|---|---|---|---|---|---|---|---|---|---|---|---|---|---|---|---|
| 1 | | | | 5 | | | | | 10 | | | | | 15 | |

| Arg | Gly | Arg | Ser | Ala | Ala | Pro | Glu | Arg | Met | Thr | Gly | Ala | Gln | Ala | Ile |
| | | | 20 | | | | | 25 | | | | | 30 | | |

| Val | Arg | Ser | Leu | Glu | Glu | Leu | Asn | Ala | Asp | Ile | Val | Phe | Gly | Ile | Pro |
| | | 35 | | | | | 40 | | | | | 45 | | | |

| Gly | Gly | Ala | Val | Leu | Pro | Val | Tyr | Asp | Pro | Leu | Tyr | Ser | Ser | Thr | Lys |
| | 50 | | | | | 55 | | | | | 60 | | | | |

| Val | Arg | His | Val | Leu | Val | Arg | His | Glu | Gln | Gly | Ala | Gly | His | Ala | Ala |
| 65 | | | | | 70 | | | | | 75 | | | | | 80 |

| Thr | Gly | Tyr | Ala | Gln | Val | Thr | Gly | Arg | Val | Gly | Val | Cys | Ile | Ala | Ser |
| | | | | 85 | | | | | 90 | | | | | 95 | |

| Ser | Gly | Pro | Gly | Ala | Thr | Asn | Leu | Val | Thr | Pro | Ile | Ala | Asp | Ala | Asn |
| | | | 100 | | | | | 105 | | | | | 110 | | |

| Leu | Asp | Ser | Val | Pro | Met | Val | Ala | Ile | Thr | Gly | Gln | Val | Gly | Ser | Gly |
| | | 115 | | | | | 120 | | | | | 125 | | | |

| Leu | Leu | Gly | Thr | Asp | Ala | Phe | Gln | Glu | Ala | Asp | Ile | Arg | Gly | Ile | Thr |
| | 130 | | | | | 135 | | | | | 140 | | | | |

| Met | Pro | Val | Thr | Lys | His | Asn | Phe | Met | Val | Thr | Asp | Pro | Asn | Asp | Ile |
| 145 | | | | | 150 | | | | | 155 | | | | | 160 |

| Pro | Gln | Ala | Leu | Ala | Glu | Ala | Phe | His | Leu | Ala | Ile | Thr | Gly | Arg | Pro |
| | | | | 165 | | | | | 170 | | | | | 175 | |

| Gly | Pro | Val | Leu | Val | Asp | Ile | Pro | Lys | Asp | Val | Gln | Asn | Ala | Glu | Leu |
| | | | 180 | | | | | 185 | | | | | 190 | | |

| Asp | Phe | Val | Trp | Pro | Pro | Lys | Ile | Asp | Leu | Pro | Gly | Tyr | Arg | Pro | Val |
| | | 195 | | | | | 200 | | | | | 205 | | | |

| Ser | Thr | Pro | His | Ala | Arg | Gln | Ile | Glu | Gln | Ala | Val | Lys | Leu | Ile | Gly |
| | 210 | | | | | 215 | | | | | 220 | | | | |

| Glu | Ala | Lys | Lys | Pro | Val | Leu | Tyr | Ile | Gly | Gly | Gly | Val | Ile | Lys | Ala |
| 225 | | | | | 230 | | | | | 235 | | | | | 240 |

| Asp | Ala | His | Glu | Glu | Leu | Arg | Ala | Phe | Ala | Glu | Tyr | Thr | Gly | Ile | Pro |
| | | | | 245 | | | | | 250 | | | | | 255 | |

| Val | Val | Thr | Thr | Leu | Met | Ala | Leu | Gly | Thr | Phe | Pro | Glu | Ser | His | Glu |
| | | | 260 | | | | | 265 | | | | | 270 | | |

| Leu | His | Met | Gly | Met | Pro | Gly | Met | His | Gly | Thr | Val | Ser | Ala | Val | Gly |
| | | 275 | | | | | 280 | | | | | 285 | | | |

| Ala | Leu | Gln | Arg | Ser | Asp | Leu | Leu | Ile | Ala | Ile | Gly | Ser | Arg | Phe | Asp |
| | 290 | | | | | 295 | | | | | 300 | | | | |

| Asp | Arg | Val | Thr | Gly | Asp | Val | Asp | Thr | Phe | Ala | Pro | Ala | Lys | Ile |
| 305 | | | | | 310 | | | | | 315 | | | | | 320 |

| Ile | His | Ala | Asp | Ile | Asp | Pro | Ala | Glu | Ile | Gly | Lys | Ile | Lys | Gln | Val |
| | | | | 325 | | | | | 330 | | | | | 335 | |

| Glu | Val | Pro | Ile | Val | Gly | Asp | Ala | Arg | Glu | Val | Leu | Ala | Arg | Leu | Leu |
| | | | 340 | | | | | 345 | | | | | 350 | | |

Glu Thr Thr Lys Ala Ser Lys Ala Glu Thr Glu Asp Ile Ser Glu Trp
            355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
    610                 615                 620

Glu Ala
625

<210> SEQ ID NO 29
<211> LENGTH: 626
<212> TYPE: PRT
<213> ORGANISM: Artificial Sequence
<220> FEATURE:
<223> OTHER INFORMATION: T96A

<400> SEQUENCE: 29

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Gln Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

```
Thr Gly Tyr Ala Gln Val Thr Gly Arg Val Gly Val Cys Ile Ala Ala
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
130                 135                 140

Met Pro Val Thr Lys His Asn Phe Met Val Thr Asp Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Ile Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495
```

```
Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
    610                 615                 620

Glu Ala
625

<210> SEQ ID NO 30
<211> LENGTH: 626
<212> TYPE: PRT
<213> ORGANISM: Artificial Sequence
<220> FEATURE:
<223> OTHER INFORMATION: T96C

<400> SEQUENCE: 30

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Gln Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Cys
                85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asp Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220
```

```
Glu Ala Lys Lys Pro Val Leu Tyr Ile Gly Gly Val Ile Lys Ala
225                 230                 235                 240

Asp Ala His Glu Glu Leu Arg Ala Phe Ala Glu Tyr Thr Gly Ile Pro
            245                 250                 255

Val Val Thr Thr Leu Met Ala Leu Gly Thr Phe Pro Glu Ser His Glu
        260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
            325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
        450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Trp Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
        530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
            565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
            610                 615                 620

Glu Ala
625
```

<210> SEQ ID NO 31
<211> LENGTH: 626
<212> TYPE: PRT
<213> ORGANISM: Artificial Sequence
<220> FEATURE:
<223> OTHER INFORMATION: W503Q

<400> SEQUENCE: 31

```
Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Gln Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65              70                  75                  80

Thr Gly Tyr Ala Gln Val Thr Gly Arg Val Gly Val Cys Ile Ala Thr
            85                  90                  95

Ser Gly Pro Gly Ala Thr Asn Leu Val Thr Pro Ile Ala Asp Ala Asn
            100                 105                 110

Leu Asp Ser Val Pro Met Val Ala Ile Thr Gly Gln Val Gly Ser Gly
        115                 120                 125

Leu Leu Gly Thr Asp Ala Phe Gln Glu Ala Asp Ile Arg Gly Ile Thr
    130                 135                 140

Met Pro Val Thr Lys His Asn Phe Met Val Thr Asp Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Ile Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
```

370                 375                 380
Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
    530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
    610                 615                 620

Glu Ala
625

<210> SEQ ID NO 32
<211> LENGTH: 626
<212> TYPE: PRT
<213> ORGANISM: Artificial Sequence
<220> FEATURE:
<223> OTHER INFORMATION: W503N

<400> SEQUENCE: 32

Met Asn Val Ala Ala Ser Gln Gln Pro Thr Pro Ala Thr Val Ala Ser
1               5                   10                  15

Arg Gly Arg Ser Ala Ala Pro Glu Arg Met Thr Gly Ala Gln Ala Ile
            20                  25                  30

Val Arg Ser Leu Glu Glu Leu Asn Ala Asp Ile Val Phe Gly Ile Pro
        35                  40                  45

Gly Gly Ala Val Leu Pro Val Tyr Asp Pro Leu Tyr Ser Ser Thr Lys
    50                  55                  60

Val Arg His Val Leu Val Arg His Glu Gln Gly Ala Gly His Ala Ala
65                  70                  75                  80

Thr Gly Tyr Ala Gln Val Thr Gly Arg Val Gly Val Cys Ile Ala Thr
                85                  90                  95

Ser Gly Pro Gly Ala Thr Asn Leu Val Thr Pro Ile Ala Asp Ala Asn

-continued

```
                100                 105                 110
Leu Asp Ser Val Pro Met Val Ala Ile Thr Gly Gln Val Gly Ser Gly
            115                 120                 125

Leu Leu Gly Thr Asp Ala Phe Gln Glu Ala Asp Ile Arg Gly Ile Thr
        130                 135                 140

Met Pro Val Thr Lys His Asn Phe Met Val Thr Asp Pro Asn Asp Ile
145                 150                 155                 160

Pro Gln Ala Leu Ala Glu Ala Phe His Leu Ala Ile Thr Gly Arg Pro
                165                 170                 175

Gly Pro Val Leu Val Asp Ile Pro Lys Asp Val Gln Asn Ala Glu Leu
            180                 185                 190

Asp Phe Val Trp Pro Pro Lys Ile Asp Leu Pro Gly Tyr Arg Pro Val
        195                 200                 205

Ser Thr Pro His Ala Arg Gln Ile Glu Gln Ala Val Lys Leu Ile Gly
    210                 215                 220

Glu Ala Lys Lys Pro Val Leu Tyr Ile Gly Gly Gly Val Ile Lys Ala
225                 230                 235                 240

Asp Ala His Glu Glu Leu Arg Ala Phe Ala Glu Tyr Thr Gly Ile Pro
                245                 250                 255

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
    290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
    370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Gly Leu Gly Thr Met Gly Tyr Ala Val Pro Ala
        435                 440                 445

Ala Leu Gly Ala Lys Ala Gly Ala Pro Asp Lys Glu Val Trp Ala Ile
    450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Asn Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525
```

-continued

```
Thr Leu Ser Glu Gly Leu Gly Cys Val Ala Ile Arg Val Thr Lys Ala
    530                 535                 540
Glu Glu Val Leu Pro Ala Ile Gln Lys Ala Arg Glu Ile Asn Asp Arg
545                 550                 555                 560
Pro Val Val Ile Asp Phe Ile Val Gly Glu Asp Ala Gln Val Trp Pro
                565                 570                 575
Met Val Ser Ala Gly Ser Ser Asn Ser Asp Ile Gln Tyr Ala Leu Gly
            580                 585                 590
Leu Arg Pro Phe Phe Asp Gly Asp Glu Ser Ala Ala Glu Asp Pro Ala
        595                 600                 605
Asp Ile His Glu Ala Val Ser Asp Ile Asp Ala Ala Val Glu Ser Thr
    610                 615                 620
Glu Ala
625

<210> SEQ ID NO 33
<211> LENGTH: 626
<212> TYPE: PRT
<213> ORGANISM: Artificial Sequence
<220> FEATURE:
<223> OTHER INFORMATION: W503L

<400> SEQUENCE: 33

Met Asn Val Ala Ala Ser Gln Gln Pro Thr Pro Ala Thr Val Ala Ser
1               5                   10                  15
Arg Gly Arg Ser Ala Ala Pro Glu Arg Met Thr Gly Ala Gln Ala Ile
            20                  25                  30
Val Arg Ser Leu Glu Glu Leu Asn Ala Asp Ile Val Phe Gly Ile Pro
        35                  40                  45
Gly Gly Ala Val Leu Pro Val Tyr Asp Pro Leu Tyr Ser Ser Thr Lys
    50                  55                  60
Val Arg His Val Leu Val Arg His Glu Gln Gly Ala Gly His Ala Ala
65                  70                  75                  80
Thr Gly Tyr Ala Gln Val Thr Gly Arg Val Gly Val Cys Ile Ala Thr
                85                  90                  95
Ser Gly Pro Gly Ala Thr Asn Leu Val Thr Pro Ile Ala Asp Ala Asn
            100                 105                 110
Leu Asp Ser Val Pro Met Val Ala Ile Thr Gly Gln Val Gly Ser Gly
        115                 120                 125
Leu Leu Gly Thr Asp Ala Phe Gln Glu Ala Asp Ile Arg Gly Ile Thr
    130                 135                 140
Met Pro Val Thr Lys His Asn Phe Met Val Thr Asp Pro Asn Asp Ile
145                 150                 155                 160
Pro Gln Ala Leu Ala Glu Ala Phe His Leu Ala Ile Thr Gly Arg Pro
                165                 170                 175
Gly Pro Val Leu Val Asp Ile Pro Lys Asp Val Gln Asn Ala Glu Leu
            180                 185                 190
Asp Phe Val Trp Pro Pro Lys Ile Asp Leu Pro Gly Tyr Arg Pro Val
        195                 200                 205
Ser Thr Pro His Ala Arg Gln Ile Glu Gln Ala Val Lys Leu Ile Gly
    210                 215                 220
Glu Ala Lys Lys Pro Val Leu Tyr Ile Gly Gly Val Ile Lys Ala
225                 230                 235                 240
Asp Ala His Glu Glu Leu Arg Ala Phe Ala Glu Tyr Thr Gly Ile Pro
                245                 250                 255
```

Val Val Thr Thr Leu Met Ala Leu Gly Thr Phe Pro Glu Ser His Glu
            260                 265                 270

Leu His Met Gly Met Pro Gly Met His Gly Thr Val Ser Ala Val Gly
        275                 280                 285

Ala Leu Gln Arg Ser Asp Leu Leu Ile Ala Ile Gly Ser Arg Phe Asp
        290                 295                 300

Asp Arg Val Thr Gly Asp Val Asp Thr Phe Ala Pro Asp Ala Lys Ile
305                 310                 315                 320

Ile His Ala Asp Ile Asp Pro Ala Glu Ile Gly Lys Ile Lys Gln Val
                325                 330                 335

Glu Val Pro Ile Val Gly Asp Ala Arg Glu Val Leu Ala Arg Leu Leu
            340                 345                 350

Glu Thr Thr Lys Ala Ser Lys Ala Glu Thr Glu Asp Ile Ser Glu Trp
        355                 360                 365

Val Asp Tyr Leu Lys Gly Leu Lys Ala Arg Phe Pro Arg Gly Tyr Asp
370                 375                 380

Glu Gln Pro Gly Asp Leu Leu Ala Pro Gln Phe Val Ile Glu Thr Leu
385                 390                 395                 400

Ser Lys Glu Val Gly Pro Asp Ala Ile Tyr Cys Ala Gly Val Gly Gln
                405                 410                 415

His Gln Met Trp Ala Ala Gln Phe Val Asp Phe Glu Lys Pro Arg Thr
            420                 425                 430

Trp Leu Asn Ser Gly Leu Gly Thr Met Gly Tyr Ala Val Pro Ala Ala
        435                 440                 445

Ala Leu Gly Ala Lys Ala Gly Ala Pro Asp Lys Glu Val Trp Ala Ile
        450                 455                 460

Asp Gly Asp Gly Cys Phe Gln Met Thr Asn Gln Glu Leu Thr Thr Ala
465                 470                 475                 480

Ala Val Glu Gly Phe Pro Ile Lys Ile Ala Leu Ile Asn Asn Gly Asn
                485                 490                 495

Leu Gly Met Val Arg Gln Leu Gln Thr Leu Phe Tyr Glu Gly Arg Tyr
            500                 505                 510

Ser Asn Thr Lys Leu Arg Asn Gln Gly Glu Tyr Met Pro Asp Phe Val
        515                 520                 525

Thr Leu Ser Glu Gly Leu Gly Cys Val Ala Ile Arg Val Thr Lys Ala
        530                 535                 540

Glu Glu Val Leu Pro Ala Ile Gln Lys Ala Arg Glu Ile Asn Asp Arg
545                 550                 555                 560

Pro Val Val Ile Asp Phe Ile Val Gly Glu Asp Ala Gln Val Trp Pro
                565                 570                 575

Met Val Ser Ala Gly Ser Ser Asn Ser Asp Ile Gln Tyr Ala Leu Gly
            580                 585                 590

Leu Arg Pro Phe Phe Asp Gly Asp Glu Ser Ala Ala Glu Asp Pro Ala
        595                 600                 605

Asp Ile His Glu Ala Val Ser Asp Ile Asp Ala Ala Val Glu Ser Thr
        610                 615                 620

Glu Ala
625

<210> SEQ ID NO 34
<211> LENGTH: 1881
<212> TYPE: DNA
<213> ORGANISM: Artificial Sequence
<220> FEATURE:

<223> OTHER INFORMATION: T96S

<400> SEQUENCE: 34

```
gtgaatgtgg cagcttctca acagcccact cccgccacgg ttgcaagccg tggtcgatcc      60
gccgcccctg agcggatgac aggtgcacag gcaattgttc gatcgctcga ggagcttaac     120
gccgacatcg tgttcggtat tcctggtggt gcggtgctac cggtgtatga cccgctctat     180
tcctccacaa aggtgcgcca cgtcctggtg cgccacgagc agggcgcagg ccacgcagca     240
accggctacg cgcaggttac tggacgcgtt ggcgtctgca ttgcatcctc tggcccaggc     300
gcaaccaact tggttacccc aatcgctgat gcaaacttgg actccgttcc catggttgcc     360
atcaccggcc aggtcggaag tggcctgctg ggtaccgatg ctttccagga agccgatatc     420
cgcggcatca ccatgccagt gaccaagcac aacttcatgg tcaccgaccc caacgacatt     480
ccacaggcat tggctgaggc attccacctc gcgattactg gtcgccctgg ccctgttctg     540
gtggatattc ctaaggatgt ccaaaacgct gaattggatt tcgtctggcc accaaagatc     600
gacctgccag gctaccgccc agtttctact ccgcatgctc gacagattga gcaggctgtc     660
aaactgatcg tgaagccaa aaagccagtc ctttacattg gcggcggcgt tatcaaggct     720
gatgcacacg aagaactgcg tgcatttgct gagtacaccg gcatcccagt tgtcaccacc     780
ttgatggcat tgggtacctt cccagagtcc cacgagctgc acatgggtat gccaggcatg     840
cacggcaccg tgtccgctgt tggcgcactg cagcgcagtg acctgctgat tgctatcggt     900
tcccgcttcg acgaccgcgt caccggtgac gttgacacct tcgcacctga tgccaagatc     960
attcacgctg acattgatcc tgccgaaatc ggcaagatca gcaggttgaa ggttccaatc    1020
gtgggcgatg cccgcgaggt tcttgctcgt ctgctggaaa ccaccaaggc aagcaaggca    1080
gagaccgagg acatctccga gtgggttgat tacctcaagg gcctcaaggc acgtttccca    1140
cgtggctacg acgagcagcc aggcgatctg ctggccacca gtttgtcat tgaaaccctg    1200
tccaaggaag ttggccccga cgcaatttac tgcgccggcg ttggccagca ccagatgtgg    1260
gcagctcagt tcgttgactt tgaaaagcca cgcacctggc tcaactctgg cggcctgggc    1320
accatgggct acgcagttcc tgcggctctt ggagcaaagg ctggcgcacc tgacaaggaa    1380
gtctgggcta tcgacggcga cggctgtttc cagatgacca accaggaact caccaccgcc    1440
gcagttgaag gtttccccat taagatcgca ctaatcaaca acggaaacct gggcatggtt    1500
cgccaatggc agaccctatt ctatgaagga cggtactcaa atactaaact tcgtaaccag    1560
ggcgagtaca tgcccgactt tgttacccct tctgagggac ttggctgtgt tgccatccgc    1620
gtcaccaaag cggaggaagt actgccagcc atccaaaagg ctcgagagat caacgaccgc    1680
ccagtagtca tcgacttcat cgtcggtgaa gacgcacagg tatggccaat ggtgtctgct    1740
ggatcatcca actccgatat ccagtacgca ctcggattgc gcccattctt tgatggtgat    1800
gaatctgcag cagaagatcc tgccgacatt cacgaagccg tcagcgacat tgatgccgcc    1860
gttgaatcga ccgaggcata a                                             1881
```

<210> SEQ ID NO 35
<211> LENGTH: 1881
<212> TYPE: DNA
<213> ORGANISM: Artificial Sequence
<220> FEATURE:
<223> OTHER INFORMATION: T96A

<400> SEQUENCE: 35

```
gtgaatgtgg cagcttctca acagcccact cccgccacgg ttgcaagccg tggtcgatcc      60
```

```
gccgcccctg agcggatgac aggtgcacag gcaattgttc gatcgctcga ggagcttaac    120
gccgacatcg tgttcggtat tcctggtggt gcggtgctac cggtgtatga cccgctctat    180
tcctccacaa aggtgcgcca cgtcctggtg cgccacgagc agggcgcagg ccacgcagca    240
accggctacg cgcaggttac tggacgcgtt ggcgtctgca ttgcagcatc tggcccaggc    300
gcaaccaact tggttacccc aatcgctgat gcaaacttgg actccgttcc catggttgcc    360
atcaccggcc aggtcggaag tggcctgctg ggtaccgatg ctttccagga agccgatatc    420
cgcggcatca ccatgccagt gaccaagcac aacttcatgg tcaccgaccc caacgacatt    480
ccacaggcat tggctgaggc attccacctc gcgattactg gtcgccctgg ccctgttctg    540
gtggatattc ctaaggatgt ccaaaacgct gaattggatt tcgtctggcc accaaagatc    600
gacctgccag gctaccgccc agtttctact ccgcatgctc gacagattga gcaggctgtc    660
aaactgatcg gtgaagccaa aaagccagtc ctttacattg gcggcggcgt tatcaaggct    720
gatgcacacg aagaactgcg tgcatttgct gagtacaccg gcatcccagt tgtcaccacc    780
ttgatggcat tgggtacctt cccagagtcc cacgagctgc acatgggtat gccaggcatg    840
cacggcaccg tgtccgctgt tggcgcactg cagcgcagtg acctgctgat tgctatcggt    900
tcccgcttcg acgaccgcgt caccggtgac gttgacacct tcgcacctga tgccaagatc    960
attcacgctg acattgatcc tgccgaaatc ggcaagatca agcaggttga ggttccaatc    1020
gtgggcgatg cccgcgaggt tcttgctcgt ctgctggaaa ccaccaaggc aagcaaggca    1080
gagaccgagg acatctccga gtgggttgat tacctcaagg gcctcaaggc acgtttccca    1140
cgtggctacg acgagcagcc aggcgatctg ctggcaccac agtttgtcat tgaaaccctg    1200
tccaaggaag ttggccccga cgcaatttac tgcgccggcg ttggccagca ccagatgtgg    1260
gcagctcagt tcgttgactt tgaaaagcca cgcacctggc tcaactctgg cggcctgggc    1320
accatgggct acgcagttcc tgcggctctt ggagcaaagg ctggcgcacc tgacaaggaa    1380
gtctgggcta tcgacggcga cggctgtttc cagatgacca accaggaact caccaccgcc    1440
gcagttgaag gtttccccat taagatcgca ctaatcaaca cggaaacct gggcatggtt    1500 cgccaatggc agaccctatt ctatgaagga cggtactcaa atactaaact tcgtaaccag    1560
ggcgagtaca tgcccgactt tgttacccct tctgagggac ttggctgtgt tgccatccgc    1620
gtcaccaaag cggaggaagt actgccagcc atccaaaagg ctcgagagat caacgaccgc    1680
ccagtagtca tcgacttcat cgtcggtgaa gacgcacagg tatggccaat ggtgtctgct    1740
ggatcatcca actccgatat ccagtacgca ctcggattgc gcccattctt tgatggtgat    1800
gaatctgcag cagaagatcc tgccgacatt cacgaagccg tcagcgacat tgatgccgcc    1860
gttgaatcga ccgaggcata a                                              1881

<210> SEQ ID NO 36
<211> LENGTH: 1881
<212> TYPE: DNA
<213> ORGANISM: Artificial Sequence
<220> FEATURE:
<223> OTHER INFORMATION: T96C

<400> SEQUENCE: 36
gtgaatgtgg cagcttctca acagcccact cccgccacgg ttgcaagccg tggtcgatcc     60
gccgcccctg agcggatgac aggtgcacag gcaattgttc gatcgctcga ggagcttaac    120
gccgacatcg tgttcggtat tcctggtggt gcggtgctac cggtgtatga cccgctctat    180
```

```
tcctccacaa aggtgcgcca cgtcctggtg cgccacgagc agggcgcagg ccacgcagca      240
accggctacg cgcaggttac tggacgcgtt ggcgtctgca ttgcatgctc tggcccaggc      300
gcaaccaact tggttacccc aatcgctgat gcaaacttgg actccgttcc catggttgcc      360
atcaccggcc aggtcggaag tggcctgctg ggtaccgatg ctttccagga agccgatatc      420
cgcggcatca ccatgccagt gaccaagcac aacttcatgg tcaccgaccc caacgacatt      480
ccacaggcat ggctgaggc attccacctc gcgattactg gtcgccctgg ccctgttctg       540
gtggatattc ctaaggatgt ccaaaacgct gaattggatt tcgtctggcc accaaagatc      600
gacctgccag ctaccgccc agtttctact ccgcatgctc gacagattga gcaggctgtc       660
aaactgatcg gtgaagccaa aaagccagtc ctttacattg gcggcggcgt tatcaaggct      720
gatgcacacg aagaactgcg tgcatttgct gagtacaccg gcatcccagt tgtcaccacc      780
ttgatggcat tgggtaccct tccagagtcc cacgagctgc acatgggtat gccaggcatg      840
cacggcaccg tgtccgctgt tggcgcactg cagcgcagtg acctgctgat tgctatcggt      900
tcccgcttcg acgaccgcgt caccggtgac gttgacacct tcgcacctga tgccaagatc      960
attcacgctg acattgatcc tgccgaaatc ggcaagatca agcaggttga ggttccaatc     1020
gtgggcgatg cccgcgaggt tcttgctcgt ctgctggaaa ccaccaaggc aagcaaggca     1080
gagaccgagg acatctccga gtgggttgat tacctcaagg gcctcaaggc acgtttccca     1140
cgtggctacg acgagcagcc aggcgatctg ctggcaccac agtttgtcat tgaaaccctg     1200
tccaaggaag ttggccccga cgcaatttac tgcgccggcg ttggccagca ccagatgtgg     1260
gcagctcagt tcgttgactt tgaaaagcca cgcacctggc tcaactctgg cggcctgggc     1320
accatgggct acgcagttcc tgcggctctt ggagcaaagg ctggcgcacc tgacaaggaa     1380
gtctgggcta cgacggcga cggctgtttc cagatgacca accaggaact caccaccgcc     1440
gcagttgaag gtttccccat taagatcgca ctaatcaaca cggaaacct gggcatggtt      1500 cgccaatggc agaccctatt ctatgaagga cggtactcaa atactaaact tcgtaaccag     1560
ggcgagtaca tgcccgactt tgttacccct tctgagggac ttggctgtgt tgccatccgc     1620
gtcaccaaag cggaggaagt actgccagcc atccaaaagg ctcgagagat caacgaccgc     1680
ccagtagtca tcgacttcat cgtcggtgaa gacgcacagg tatggccaat ggtgtctgct     1740
ggatcatcca actccgatat ccagtacgca ctcggattgc gcccattctt tgatggtgat     1800
gaatctgcag cagaagatcc tgccgacatt cacgaagccg tcagcgacat tgatgccgcc     1860
gttgaatcga ccgaggcata a                                               1881

<210> SEQ ID NO 37
<211> LENGTH: 1881
<212> TYPE: DNA
<213> ORGANISM: Artificial Sequence
<220> FEATURE:
<223> OTHER INFORMATION: W503Q

<400> SEQUENCE: 37
gtgaatgtgg cagcttctca acagcccact cccgccacgg ttgcaagccg tggtcgatcc       60 gccgccctg agcggatgac aggtgcacag gcaattgttc gatcgctcga ggagcttaac       120
gccgacatcg tgttcggtat tcctggtggt gcggtgctac cggtgtatga cccgctctat      180
tcctccacaa aggtgcgcca cgtcctggtg cgccacgagc agggcgcagg ccacgcagca      240
accggctacg cgcaggttac tggacgcgtt ggcgtctgca ttgcaacctc tggcccaggc      300
gcaaccaact tggttacccc aatcgctgat gcaaacttgg actccgttcc catggttgcc      360
```

```
atcaccggcc aggtcggaag tggcctgctg ggtaccgatg ctttccagga agccgatatc    420
cgcggcatca ccatgccagt gaccaagcac aacttcatgg tcaccgaccc caacgacatt    480
ccacaggcat tggctgaggc attccacctc gcgattactg tcgccctgg ccctgttctg     540 gtggatattc ctaaggatgt ccaaaacgct gaattggatt tcgtctggcc accaaagatc    600
gacctgccag gctaccgccc agtttctact ccgcatgctc gacagattga gcaggctgtc    660
aaactgatcg gtgaagccaa aaagccagtc ctttacattg gcggcggcgt tatcaaggct    720
gatgcacacg aagaactgcg tgcatttgct gagtacaccg gcatcccagt tgtcaccacc    780
ttgatggcat gggtaccttc ccagagtcc acgagctgc acatgggtat gccaggcatg      840
cacggcaccg tgtccgctgt tggcgcactg cagcgcagtg acctgctgat tgctatcggt    900
tcccgcttcg acgaccgcgt caccggtgac gttgacacct cgcacctga tgccaagatc     960 attcacgctg acattgatcc tgccgaaatc ggcaagatca agcaggttga ggttccaatc   1020
gtgggcgatg cccgcgaggt tcttgctcgt ctgctggaaa ccaccaaggc aagcaaggca   1080
gagaccgagg acatctccga gtgggttgat tacctcaagg gcctcaaggc acgtttccca   1140
cgtggctacg acgagcagcc aggcgatctg ctggcaccac agtttgtcat tgaaaccctg   1200
tccaaggaag ttggccccga cgcaatttac tgcgccggcg ttggccagca ccagatgtgg   1260
gcagctcagt tcgttgactt tgaaaagcca cgcacctggc tcaactctgg cggcctgggc   1320
accatgggct acgcagttcc tgcggctctt ggagcaaagg ctggcgcacc tgacaaggaa   1380
gtctgggcta tcgacggcga cggctgtttc cagatgacca accaggaact caccaccgcc   1440
gcagttgaag gtttccccat taagatcgca ctaatcaaca acggaaacct gggcatggtt   1500
cgccaacagc agaccctatt ctatgaagga cggtactcaa atactaaact tcgtaaccag   1560
ggcgagtaca tgcccgactt tgttacccctt tctgagggac ttggctgtgt tgccatccgc   1620
gtcaccaaag cggaggaagt actgccagcc atccaaaagg ctcgagagat caacgaccgc   1680
ccagtagtca tcgacttcat cgtcggtgaa gacgcacagg tatggccaat ggtgtctgct   1740
ggatcatcca actccgatat ccagtacgca ctcggattgc gcccattctt tgatggtgat   1800
gaatctgcag cagaagatcc tgccgacatt cacgaagccg tcagcgacat tgatgccgcc   1860
gttgaatcga ccgaggcata a                                             1881
```

<210> SEQ ID NO 38
<211> LENGTH: 1881
<212> TYPE: DNA
<213> ORGANISM: Artificial Sequence
<220> FEATURE:
<223> OTHER INFORMATION: W503N

<400> SEQUENCE: 38

```
gtgaatgtgg cagcttctca acagcccact cccgccacgg ttgcaagccg tggtcgatcc      60 gccgccctg agcggatgac aggtgcacag gcaattgttc gatcgctcga ggagcttaac      120
gccgacatcg tgttcggtat tcctggtggt gcggtgctac cggtgtatga cccgctctat     180
tcctccacaa aggtgcgcca cgtcctggtg cgccacgagc agggcgcagg ccacgcagca     240
accggctacg cgcaggttac tggacgcgtt ggcgtctgca ttgcaacctc tggcccaggc     300
gcaaccaact tggttacccc aatcgctgat gcaaacttgg actccgttcc catggttgcc     360
atcaccggcc aggtcggaag tggcctgctg ggtaccgatg ctttccagga agccgatatc     420
cgcggcatca ccatgccagt gaccaagcac aacttcatgg tcaccgaccc caacgacatt     480
```

| | |
|---|---:|
| ccacaggcat tggctgaggc attccacctc gcgattactg gtcgccctgg ccctgttctg | 540 |
| gtggatattc ctaaggatgt ccaaaacgct gaattggatt tcgtctggcc accaaagatc | 600 |
| gacctgccag gctaccgccc agtttctact ccgcatgctc gacagattga gcaggctgtc | 660 |
| aaactgatcg gtgaagccaa aaagccagtc ctttacattg gcggcggcgt tatcaaggct | 720 |
| gatgcacacg aagaactgcg tgcatttgct gagtacaccg gcatcccagt tgtcaccacc | 780 |
| ttgatggcat gggtaccttc ccagagtcc cacgagctgc acatgggtat gccaggcatg | 840 |
| cacggcaccg tgtccgctgt tggcgcactg cagcgcagtg acctgctgat tgctatcggt | 900 |
| tcccgcttcg acgaccgcgt caccggtgac gttgacacct tcgcacctga tgccaagatc | 960 |
| attcacgctg acattgatcc tgccgaaatc ggcaagatca agcaggttga ggttccaatc | 1020 |
| gtgggcgatg cccgcgaggt tcttgctcgt ctgctggaaa ccaccaaggc aagcaaggca | 1080 |
| gagaccgagg acatctccga gtgggttgat tacctcaagg gcctcaaggc acgtttccca | 1140 |
| cgtggctacg acgagcagcc aggcgatctg ctggcaccac agtttgtcat tgaaaccctg | 1200 |
| tccaaggaag ttggccccga cgcaatttac tgcgccggcg ttggccagca ccagatgtgg | 1260 |
| gcagctcagt tcgttgactt tgaaaagcca cgcacctggc tcaactctgg cggcctgggc | 1320 |
| accatgggct acgcagttcc tgcggctctt ggagcaaagg ctggcgcacc tgacaaggaa | 1380 |
| gtctgggcta cgacggcga cggctgtttc cagatgacca accaggaact caccaccgcc | 1440 |
| gcagttgaag gtttccccat taagatcgca ctaatcaaca cgaaaacct gggcatggtt | 1500 |
| cgccaaaacc agaccctatt ctatgaagga cggtactcaa atactaaact tcgtaaccag | 1560 |
| ggcgagtaca tgcccgactt tgttacccctt tctgagggac ttggctgtgt tgccatccgc | 1620 |
| gtcaccaaag cggaggaagt actgccagcc atccaaaagg ctcgagagat caacgaccgc | 1680 |
| ccagtagtca tcgacttcat cgtcggtgaa gacgcacagg tatggccaat ggtgtctgct | 1740 |
| ggatcatcca actccgatat ccagtacgca ctcggattgc gcccattctt tgatggtgat | 1800 |
| gaatctgcag cagaagatcc tgccgacatt cacgaagccg tcagcgacat tgatgccgcc | 1860 |
| gttgaatcga ccgaggcata a | 1881 |

<210> SEQ ID NO 39
<211> LENGTH: 1881
<212> TYPE: DNA
<213> ORGANISM: Artificial Sequence
<220> FEATURE:
<223> OTHER INFORMATION: W503L

<400> SEQUENCE: 39

| | |
|---|---:|
| gtgaatgtgg cagcttctca acagcccact cccgccacgg ttgcaagccg tggtcgatcc | 60 |
| gccgcccctg agcggatgac aggtgcacag gcaattgttc gatcgctcga ggagcttaac | 120 |
| gccgacatcg tgttcggtat tcctggtggt gcggtgctac cggtgtatga cccgctctat | 180 |
| tcctccacaa aggtgcgcca cgtcctggtg cgccacgagc agggcgcagg ccacgcagca | 240 |
| accggctacg cgcaggttac tggacgcgtt ggcgtctgca ttgcaacctc tggcccaggc | 300 |
| gcaaccaact tggttacccc aatcgctgat gcaaacttgg actccgttcc catggttgcc | 360 |
| atcaccggcc aggtcggaag tggcctgctg gtaccgatg ctttccagga agccgatatc | 420 |
| cgcggcatca ccatgccagt gaccaagcac aacttcatgg tcaccgaccc caacgacatt | 480 |
| ccacaggcat tggctgaggc attccacctc gcgattactg gtcgccctgg ccctgttctg | 540 |
| gtggatattc ctaaggatgt ccaaaacgct gaattggatt tcgtctggcc accaaagatc | 600 |
| gacctgccag gctaccgccc agtttctact ccgcatgctc gacagattga gcaggctgtc | 660 |

```
aaactgatcg gtgaagccaa aaagccagtc ctttacattg gcggcggcgt tatcaaggct    720
gatgcacacg aagaactgcg tgcatttgct gagtacaccg gcatcccagt tgtcaccacc    780
ttgatggcat tgggtacctt cccagagtcc cacgagctgc acatgggtat gccaggcatg    840
cacggcaccg tgtccgctgt tggcgcactg cagcgcagtg acctgctgat tgctatcggt    900
tcccgcttcg acgaccgcgt caccggtgac gttgacacct tcgcacctga tgccaagatc    960
attcacgctg acattgatcc tgccgaaatc ggcaagatca agcaggttga ggttccaatc   1020
gtgggcgatg cccgcgaggt tcttgctcgt ctgctggaaa ccaccaaggc aagcaaggca   1080
gagaccgagg acatctccga gtgggttgat tacctcaagg gcctcaaggc acgtttccca   1140
cgtggctacg acgagcagcc aggcgatctg ctggcaccac agtttgtcat tgaaaccctg   1200
tccaaggaag ttggccccga cgcaatttac tgcgccggcg ttggccagca ccagatgtgg   1260
gcagctcagt tcgttgactt tgaaaagcca cgcacctggc tcaactctgg cggcctgggc   1320
accatgggct acgcagttcc tgcggctctt ggagcaaagg ctggcgcacc tgacaaggaa   1380
gtctgggcta tcgacggcga cggctgtttc cagatgacca accaggaact caccaccgcc   1440
gcagttgaag gtttccccat taagatcgca ctaatcaaca acggaaacct gggcatggtt   1500
cgccaactgc agaccctatt ctatgaagga cggtactcaa atactaaact tcgtaaccag   1560
ggcgagtaca tgcccgactt tgttaccctt tctgagggac ttggctgtgt tgccatccgc   1620
gtcaccaaag cggaggaagt actgccagcc atccaaaagg ctcgagagat caacgaccgc   1680
ccagtagtca tcgacttcat cgtcggtgaa gacgcacagg tatggccaat ggtgtctgct   1740
ggatcatcca actccgatat ccagtacgca ctcggattgc gcccattctt tgatggtgat   1800
gaatctgcag cagaagatcc tgccgacatt cacgaagccg tcagcgacat tgatgccgcc   1860
gttgaatcga ccgaggcata a                                             1881
```